US008828680B2

(12) United States Patent
Williams et al.

(10) Patent No.: US 8,828,680 B2
(45) Date of Patent: Sep. 9, 2014

(54) COMBINED RAPID SUSCEPTIBILITY ASSAY AND MICROORGANISM IDENTIFICATION SYSTEM

(75) Inventors: Gregory B. Williams, Davis, CA (US); Daniel M. Nothaft, Vacaville, CA (US); Glenn F. Enscoe, Antelope, CA (US); Kathleen N. Burtner, Elk Grove, CA (US); Monte E. Kangas, Fairfield, CA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 0 days.

(21) Appl. No.: 13/402,445

(22) Filed: Feb. 22, 2012

(65) Prior Publication Data

US 2012/0149599 A1 Jun. 14, 2012

Related U.S. Application Data

(60) Division of application No. 10/967,062, filed on Oct. 15, 2004, now abandoned, which is a continuation of application No. 09/553,223, filed on Apr. 20, 2000, now abandoned.

(60) Provisional application No. 60/137,819, filed on May 27, 1999, provisional application No. 60/131,829, filed on Apr. 29, 1999.

(51) Int. Cl.
*C12Q 1/02* (2006.01)
*C12Q 1/04* (2006.01)
*C12Q 1/18* (2006.01)
*G01N 35/02* (2006.01)
*G01N 35/00* (2006.01)

(52) U.S. Cl.
CPC ...... *G01N 35/028* (2013.01); *G01N 2035/0097* (2013.01); *G01N 2035/0093* (2013.01); *G01N 35/0092* (2013.01)
USPC ......... 435/29; 435/4; 435/32; 435/34; 506/10

(58) Field of Classification Search
None
See application file for complete search history.

(56) References Cited

U.S. PATENT DOCUMENTS

| | | |
|---|---|---|
| 3,083,145 A | 3/1963 | Ryan |
| 3,088,875 A | 5/1963 | Fisk |
| 3,236,732 A | 2/1966 | Arquilla |
| 3,551,555 A | 12/1970 | Harmanus et al. |
| 3,763,734 A | 10/1973 | Meyer et al. |
| 3,832,532 A | 8/1974 | Praglin et al. |
| 3,857,931 A | 12/1974 | Hager |
| 3,895,661 A | 7/1975 | Praglin et al. |
| 3,901,588 A | 8/1975 | Longhenry |
| 3,925,166 A | 12/1975 | Blume |
| 3,928,140 A | 12/1975 | Wyatt et al. |
| 3,942,899 A | 3/1976 | Longhenry |
| 3,957,583 A | 5/1976 | Gibson et al. |
| 3,963,355 A | 6/1976 | Aldridge, Jr. et al. |
| 4,010,383 A | 3/1977 | Grassmann |
| 4,018,652 A | 4/1977 | Lanham et al. |
| 4,090,920 A | 5/1978 | Studer, Jr. |
| 4,101,383 A | 7/1978 | Wyatt et al. |
| 4,116,775 A | 9/1978 | Charles et al. |
| 4,118,280 A | 10/1978 | Charles et al. |
| 4,153,512 A | 5/1979 | Messner et al. |
| 4,207,394 A | 6/1980 | Aldridge, Jr. et al. |
| 4,245,043 A | 1/1981 | Lund |
| 4,258,543 A | 3/1981 | Canevari et al. |
| 4,288,543 A | 9/1981 | Sielaff et al. |
| 4,325,910 A | 4/1982 | Jordan |
| 4,448,534 A | 5/1984 | Wertz et al. |
| 4,603,108 A | 7/1986 | Bascomb |
| 4,643,077 A | 2/1987 | Bock |
| 4,643,879 A | 2/1987 | Hanaway |
| 4,676,951 A | 6/1987 | Armes et al. |
| 4,681,741 A | 7/1987 | Hanaway |
| 4,719,087 A | 1/1988 | Hanaway |
| 4,784,947 A | 11/1988 | Noeller |
| 4,796,197 A | 1/1989 | Lissot et al. |
| 4,856,073 A | 8/1989 | Farber et al. |
| 5,026,638 A | 6/1991 | Saperstein |
| 5,055,594 A | 10/1991 | Mize |
| 5,064,756 A | 11/1991 | Carr et al. |
| 5,162,229 A | 11/1992 | Thorpe et al. |
| 5,164,301 A | 11/1992 | Thompson et al. |

(Continued)

FOREIGN PATENT DOCUMENTS

| | | |
|---|---|---|
| EP | 0091837 | 10/1983 |
| WO | 9008196 | 7/1990 |

(Continued)

OTHER PUBLICATIONS

Maiden, MFJ et al. Rapid characterization of periodontal bacterial isolates by using fluorogenic substrate tests. Journal of Clinical Microbiology. 1996. 34(2): 376-384.*
Dade Behring MicroScan®: Rapid Gram Positive Procedure Manual (Revised Oct. 1998).
Dade Behring MicroScan®: Rapid Gram Positive Procedure Manual (Revised Mar. 1997).
Dade Behring MicroScan®: Rapid Gram Positive Procedure and QC Manual (Revised Nov. 1998).
Bauer et al., Antibiotic Susceptibility Testing by a Standardized Single Disk Method; Am. J. Clin. Path.; 45 (4) 493-6, 1966.
Beckwith et al., Evaluation of the Necessity for Routine Terminal Subculturing of Blood Cultures Negative by Radiometric Methods; J. Clin. Microbiol., Jan. 1982, pp. 35-40.

(Continued)

*Primary Examiner* — Allison Ford
*Assistant Examiner* — Susan E Fernandez

(57) ABSTRACT

In response to the need for highly-sensitive antibiotic susceptibility assays and identification assays that do not require extensive incubation times, the present invention provides automated assay methods and systems that permit the determination of antibiotic susceptibilities and/or microorganism identification in a timeframe that is substantially shorter than has previously been attainable using a hybrid system that combines turbimetric and fluorescence determinations using a single, clear-plastic assay platform. Related devices, kits, and components thereof are also disclosed.

6 Claims, 4 Drawing Sheets

(56) References Cited

U.S. PATENT DOCUMENTS

| | | |
|---|---|---|
| 5,236,827 A | 8/1993 | Sussman et al. |
| 5,290,513 A | 3/1994 | Berthold et al. |
| 5,298,753 A | 3/1994 | Sonne et al. |
| 5,340,747 A | 8/1994 | Eden |
| 5,355,215 A | 10/1994 | Schroeder et al. |
| 5,374,395 A | 12/1994 | Robinson et al. |
| 5,457,030 A | 10/1995 | Badal et al. |
| 5,457,527 A | 10/1995 | Manns et al. |
| 5,487,872 A | 1/1996 | Hafeman et al. |
| 5,496,697 A | 3/1996 | Parce et al. |
| 5,501,959 A | 3/1996 | Lancaster et al. |
| 5,518,686 A | 5/1996 | Masterson et al. |
| 5,545,535 A | 8/1996 | Roth et al. |
| 5,567,598 A | 10/1996 | Stitt et al. |
| 5,573,927 A | 11/1996 | Nelson |
| 5,627,045 A | 5/1997 | Bochner et al. |
| 5,629,169 A | 5/1997 | Izraelevitz et al. |
| 5,645,800 A | 7/1997 | Masterson et al. |
| 5,648,227 A | 7/1997 | Basboli |
| 5,654,165 A | 8/1997 | Kusunoki et al. |
| 5,759,799 A | 6/1998 | Grosso |
| 5,762,873 A | 6/1998 | Fanning et al. |
| 5,789,173 A | 8/1998 | Peck et al. |
| 5,817,475 A | 10/1998 | Gibbs et al. |
| 5,853,666 A | 12/1998 | Seaton et al. |
| 5,856,193 A | 1/1999 | Fanning et al. |
| 5,858,693 A | 1/1999 | Cottingham |
| 5,858,801 A | 1/1999 | Brizzolara |
| 5,863,752 A | 1/1999 | Court et al. |
| 5,863,754 A | 1/1999 | Bajard |
| 5,876,959 A | 3/1999 | Kusunoki et al. |
| 5,888,455 A | 3/1999 | Seaton et al. |
| 5,888,760 A | 3/1999 | Godsey et al. |
| 5,888,825 A | 3/1999 | Carr et al. |
| 5,895,751 A | 4/1999 | Hattori et al. |
| 5,962,250 A | 10/1999 | Gavin et al. |
| 5,965,090 A | 10/1999 | Fanning et al. |
| 5,985,596 A | 11/1999 | Wilson |
| 5,998,159 A | 12/1999 | Watson et al. |
| 6,027,873 A | 2/2000 | Schellenberger et al. |
| 6,030,835 A | 2/2000 | Musser et al. |
| 6,043,045 A | 3/2000 | Hoch et al. |
| 6,043,048 A | 3/2000 | Johnston et al. |
| 6,096,272 A | 8/2000 | Clark et al. |
| 6,153,400 A | 11/2000 | Matsumura et al. |
| 6,197,576 B1 | 3/2001 | Eden |

FOREIGN PATENT DOCUMENTS

| | | |
|---|---|---|
| WO | 97/44486 A1 | 11/1997 |
| WO | 98/53301 A2 | 11/1998 |
| WO | 9904228 | 1/1999 |

OTHER PUBLICATIONS

Nolte et al., Rapid and Overnight Microdilution Antibiotic Susceptibility Testing With the Sensititre Breakpoint Autoreader System; J. Clin. Microbiol. Jun. 1988, pp. 1079-1084.

Staneck et al., Automated Reading of MIC Microdilution Trays Containing Fluorogenic Enzyme Substrates With the Sensititre Autoreader; J. Clin. Microbiol. Aug. 1985, pp. 187-191.

Thornsberry et al.; Clinical Laboratory Evaluation of the Abbot MS-2 Automated Antimicrobial Susceptibility Testing System: Report of a Collaborative Study; J. Clin. Microbiol., Sep. 1980, pp. 275-390.

Fisher Biotechnology Catalog (1995) pp. 114 and 116.

Cua-Lim; Reversed BDB Technique; The Aggregation of Antibody-Coated Red Blood Cells by Homologous Antigen; J. Allergy 34: 142-154 (1968).

Gates & Tschudi; Decarboxylation and Reconstitution of Linoleic Acid; J. Am. Chem. Soc.; 74-1109 (1952).

Patil et al.; Steric Aspects of Adrenergic Drugs. I. Comparative Effects of DL Isomers and Desoxy Derivatives; The Journal of Pharmacology and Experimental Therapeutics, vol. 155, No. 1, pp. 1-12 (1967).

Ranadive et al.; Antibodies to Serotonin; Canad. J. Biochem 45; pp. 1701-1710 (1968).

Scherrer; Determination of Penicillin in Bacterial Cells by Means of Penicillin Antibodies; Pathologia et Microbiologia 26: pp. 678-687 (1963).

Stavitsky; Micromethods for the Study of Proteins and Antibodies; J. Immunol. 76: pp. 360-367 (1954).

Van Vunakis et al; Production & Specificity of Antibodies Directed Toward 3,4,5-Trimethoxyphenylethylamine, 3,4-Dimethoxyphenylethylamine and 2,5-Dimethoxy-4-Methylamphetamine; Biochem. Pharmacol 18: 393-404 (1969).

Wide & Porath; Radioimmunoassay of Proteins With the Use of Sephadex-Coupled Antibodies; Biochem. Biophys. Acta. 130: pp. 254-260 (1988).

Dade Microscan Dried Gram Negative Procedural Manual (Revised Dec. 1996).

* cited by examiner

COMBINED RAPID SUSCEPTIBILITY ASSAY AND MICROORGANISM IDENTIFICATION SYSTEM

RELATED APPLICATIONS

This application is a divisional of U.S. patent application Ser. No. 10/967,062, filed Oct. 15, 2004, which is a continuation of U.S. patent application Ser. No. 09/553,223, filed Apr. 20, 2000, the contents of which are hereby incorporated by reference in its entirety, which claims priority of provisional application Ser. No. 60/131,829 filed Apr. 29, 1999, entitled "Antibiotic Susceptibility Testing Methods and Devices" and provisional application Ser. No. 60/137,819 filed on May 27, 1999, entitled "Antibiotic Susceptibility and Microbial Identification Testing Methods and Systems".

FIELD OF THE INVENTION

A combined anti-microbial susceptibility testing and microorganism identification platform is disclosed. Specifically, the combined anti-microbial susceptibility testing and microorganism identification platform disclosed herein is a hands-free walk-away system ideally suited for clinical microbiology laboratories. More specifically, the automated, combined anti-microbial susceptibility testing and microorganism identification platform of the present invention provides anti-microbial susceptibility test results and microorganism identifications with greater accuracy and in less time than previously possible.

BACKGROUND OF THE INVENTION

The last fifty years has brought profound advances in the field of clinical microbiology and the treatment and management of infectious diseases. However, life threatening and debilitating systemic and localized microbial infections remains a major healthcare problem. Mortality resulting from infectious agents remains particularly high among infants, the elderly, the immunosuppressed, patients in long-term care facilities, and skilled nursing homes, Moreover, the emergence of multi-drug resistance organisms such as vancomycin resistant enterococci (VRE) and methacillin resistant *Staphylococcus aureaus* (MRSA) have increased the challenges of caring for hospitalized patients. Hospital acquired infections (nosocomial infections) caused by organisms such as VRE, MRSA and pseudomonas add significantly to patient suffering, increased hospital stays, iatrogenic mortality, and increased healthcare costs.

Inadequately or improperly treated microbial infections are largely responsible for the rise of multiple drug resistant strains of bacteria that cause many nosocomial infections. Drug resistance, specifically antibiotic resistance, often occurs when the antibiotic used to treat an infection is either improperly selected, prescribed in a fashion that does not effectively eradicate the infectious agent, or as a result of poor patient compliance. Furthermore, when ineffective or unnecessary antibiotics are prescribed any infecting bacteria present continues to multiply unabated often resulting in life threatening complications necessitating expensive, aggressive treatments including otherwise needless hospitalization. Therefore, the accurate and rapid diagnosis of a potential infectious agent is critical to improved patient care, reduced healthcare costs and the preservation of antimicrobial efficacy.

The first step in the proper diagnosis of a microbial infection is the determination of the causative agent. Although it is common and acceptable protocol to treat high risk patients with a broad spectrum antibiotic based on clinical judgment prior to establishing the existence, identity and susceptibility pattern of a putative infectious agent, it is still essential that such testing be conducted and treatment changed or modified as indicated by the test results.

Generally speaking, when an infection is suspected, samples are taken from the affected site and analyzed using staining techniques, genetic based assays such as the polymerase chain reaction (PCR) test and cultures. Stains can provide a skilled microscopist with reliable information about the morphology of any microorganism present and the type of cell infected. However, stains are largely non-specific and seldom definitive. Polymerase chain reaction assays are highly specific and definitive when samples are free of PCR inhibitors, contamination and contain near pure cultures of the infectious agent. However, most clinical samples taken directly from infected patients are contaminated and contain PCR inhibitors. Furthermore, PCR assays are expensive, highly specialized, and require multiple probes in order to identify an unknown organism. Consequently, PCR is seldom, if ever used to replace standard microbial culture and identification techniques as the front line test in the clinical microbiology laboratory.

While it is possible for viruses, fungi, bacteria and occasionally other microscopic life forms to cause clinical infections, the remainder of this discussion will focus on bacterial infections. This is not intended to limit the techniques and procedures disclosed herein to bacteria, but rather in deference to brevity.

Standard culture techniques rely on the use of solid nutrient media on which a clinical sample is placed, then physically diluted by spreading the sample over the solid media's surface using a sterile inoculation device such as a wire shaft terminating in a loop. The dilution process, colloquially known as "streaking," facilitates the isolation and subsequent identification of the infectious agent by permitting single bacterial cells to be separated from others present in the sample. The diluted specimen gives rise to individual cells that multiply to form a population of homogeneous prodigy organisms. The resulting population of homogeneous organisms is referred to as a colony. Samples containing only one colony type are known as pure cultures, hence, a pure culture is a population of the same species of microorganism.

It is essential that only pure cultures be tested for identity and drug susceptibility so that there are no synergistic or antagonistic effects that could result in erroneous conclusions. After a microorganism has been isolated, usually 24 to 48 hours post-inoculation, the microbiologist must identify the organism and test it for antimicrobial susceptibility.

The first step in identifying bacteria is to broadly classify the organism into one of two classes: Gram positive or Gram negative. This process is performed using a simple staining procedure or through the astute judgment of an experienced clinical microbiologist. Based on this initial classification, the microbiologist selects a panel of biochemical tests to identify the organism and chooses the panel of antimicrobials best suited to test the organism's drug susceptibility.

Traditionally, bacteria are identified by inoculation of a series of tubes containing growth media, a specific substrate, such as a sugar, and an indicator system that responds demonstrably to any affirmative action of the microorganism on the substrate. For example, if a bacteria can enzymatically degrade sugar present in a culture media, acidic by-products from the metabolism of the sugar will drop the pH of the media. This drop in pH (the acidification of the media), is detected by a change in color of a pH indicator added to the media. For example, phenol red changes from red to yellow in the presence of acid pH. These traditional growth dependent techniques require a minimum of 18-24 hours before results can be determined. Moreover, the labor and material costs associated with such methods are high, consequently only a limited number of biochemical substrates are used in the initial screen. If the results obtained after the first 18-24 hours of incubation are inconclusive, additional tests must be conducted which further delay definitive results in reaching the physician.

At the time the initial identification scheme is inoculated, the microbiologist usually initiates anti-microbial susceptibility testing. Traditionally, antimicrobial susceptibility testing is performed using liquid growth media containing predetermined concentrations of selected antibiotics, or the surface of a solid growth media is inoculated such that a confluent lawn of bacteria will develop and small disks containing an antibiotic are placed on the surface of the solid media. The liquid culture media technique is known as the broth dilution method and the inoculated solid agar procedure is referred to as the Kirby-Bauer test.

In the broth dilution test an organism is considered sensitive to the concentration of drug in the tube if the organism fails to grow in the tube, or tubes, containing the drug and thrives in a media tube with no drug present (growth control tube). There are basically two types of broth dilution susceptibility assays routinely used. One is referred to as a minimum inhibitory concentration assay (MIC), and the other is referred to as a minimum bactericidal concentration (MBC) assay. In the MIC assay an inhibitory anti-microbial compound such as an antibiotic is serially diluted (usually two-fold) in culture medium. The concentration of the drug in the last dilution where the organism fails to grow (the last no growth culture) is referred to as the minimum inhibitory concentration for that compound. A MBC assay is performed in exactly the same fashion except that the anti-microbial compounds used are known to exert a killing, rather than an inhibitory effect on an organism. An organism is considered sensitive to an anti-microbial compound when its MIC or MBC is less than an established minimum. For example, *Staphylococcus aureus* is considered sensitive to penicillin when it fails to grow in a culture containing 0.12 micrograms per milliliter or less of penicillin in the test media and resistant if the organism thrives in media containing 0.25 micrograms of penicillin per milliliter or more.

When the Kirby-Bauer is used an organism is considered sensitive to an anti-microbial compound If a zone of no growth equal to or exceeding an established minimum diameter is present around the drug-containing disk. Both the Kirby-Bauer and broth dilution methods are laborious to set up, require skilled personnel to interpret and require a minimum of 18-24 hours before results are available. Therefore, techniques and equipment that could decrease cost, increase accuracy, provide faster, more reliable results to the Physician would significantly improve patient care and reduce inappropriate and unnecessary antimicrobial therapy.

In the 1980's a variety of new technologies were introduced to clinical microbiology designed to address a number of the aforementioned problems. Most of these systems relied on conventional biochemical tests and broth dilution drug susceptibility assays that had been miniaturized and combined into single multi-well trays or plates (microtiter plates). In the miniaturized configuration each 15 mL tube of biochemical or antimicrobial used in the traditional assay was reduced in scale to a volume of approximately 200 µL. Consequently, microtiter plates containing up to 96 individual "wells" would represent 96 individual tubes in the traditional format. This resulted in an overall reduction in processing time and materials cost, but still relied on visible growth of the putative pathogen that required a minimum of 18-24 hours post-inoculation. Moreover, skilled personnel were required to read the plates. The miniaturization of the biochemical assays and drug-containing tubes from 15 mL to 200 µL resulted in difficulty reading plates because visible growth is often barely detectable. Consequently, much of the time and cost savings associated with the inoculation and set-up was lost reading and reporting results.

In an effort to increase reliability and decrease reading and reporting times associated with antimicrobial susceptibility testing, automated reading devices were developed which could detect the presence or absence of growth in a well by reading the turbidity using a spectrophotometer and comparing it to control wells. (See U.S. Pat. Nos. 4,448,534 and 3,957,583).

In addition to turbidimetric methods for determining the growth of a microorganism other techniques such as colorimetric detection systems (see U.S. Pat. No. 5,817,475) light detection and light scattering systems (see U.S. Pat. Nos. 4,118,280; 4,116,775; 3,942,899; 3,832,532; 3,901,588 and 3,928,140), pH measurements systems (see U.S. Pat. No. 5,496,697), and fluorometric and nephelometric detection systems (see U.S. Pat. No. 4,784,947) were developed. Another automated instrument for reading antimicrobial microtiter plates uses a fluorescent procedure which reads the fluorescence emitted as the result of bacterial enzymatic action on a fluorogenic substrate (see EPO 091,837 B).

In addition to systems designed to merely automate the reading and reporting steps, several different automated formats have been developed to completely automate the inoculation, incubation, reading and reporting steps associated with antimicrobial testing. Examples of such automated devices can be found in U.S. Pat. Nos. 5,645,800; 5,518,686; 4,676,951 and 4,681,741. Present automated methods for the inoculation, incubation, reading and reporting of antimicrobial susceptibility and bacterial identification have significantly advanced the reproducibility and accuracy of these assays and has decreased cost and increased throughput for the clinical laboratory. However, the aforementioned technologies all rely on a single endpoint determination based on pre-set parameters. This is especially problematic when fluorogenic substrates are used. Growth rates between different species of organisms as well as between different strains of the same species are common. In certain cases the growth rate may lag sufficiently so that when a pre-determined reading interval is reached there will be insufficient growth, and hence fluorescence to be detectable. As a result, the well will be read by the instrument as "no growth" indicating susceptibility to the respective drug at the level being tested. This in turn could be reported to the clinician that would initiate antimicrobial therapy based on an erroneous result.

Therefore, there is a need for a clinical microbiology test platform that combines anti-microbial susceptibility testing with microorganism identification. Moreover, there is a need for a combined system that generates accurate, reproducible results that are available quickly and with lower materials and labor cost than presently available.

SUMMARY OF THE INVENTION

It is an object of the present invention to provide a combined anti-microbial susceptibility and microorganism identification system.

It is another object of the present invention to provide a combined rapid anti-microbial susceptibility and microorganism identification system that is fully automated and hand-free.

It is still another object of the present invention to provide a fully automated, hands free, combined anti-microbial susceptibility and micro-organism identification system that provides, rapid, accurate, and reproducible results in a standardized format.

The present invention discloses methods of determining anti-microbial (or antibiotic) susceptibility of a variety of microorganisms, generally within a period of about 4.5-22 hours, which methods are readily and easily adapted for use in automated assays. The invention also discloses methods of determining the identity (ID) of the organism in about 2-2.5 hours.

The within-disclosed methods differ from those in the art in at least four important respects. First, a hybrid panel concept is utilized, in which samples are assayed via fluorescent as well as turbidimetric means and methods. Second, a modified clear plastic panel is disclosed for the simultaneous assay of samples via fluorescent identification (ID) and turbidimetric antimicrobial susceptibility testing (AST). Third, multiple wavelength optics (e.g. bichromatic colorimetric analysis) are used and applied to enhance sensitivity and accuracy of the assays and systems disclosed herein. Finally, novel methods of determining incubation time and susceptibility results are utilized.

DETAILED DESCRIPTION OF THE INVENTION

Figure 1:
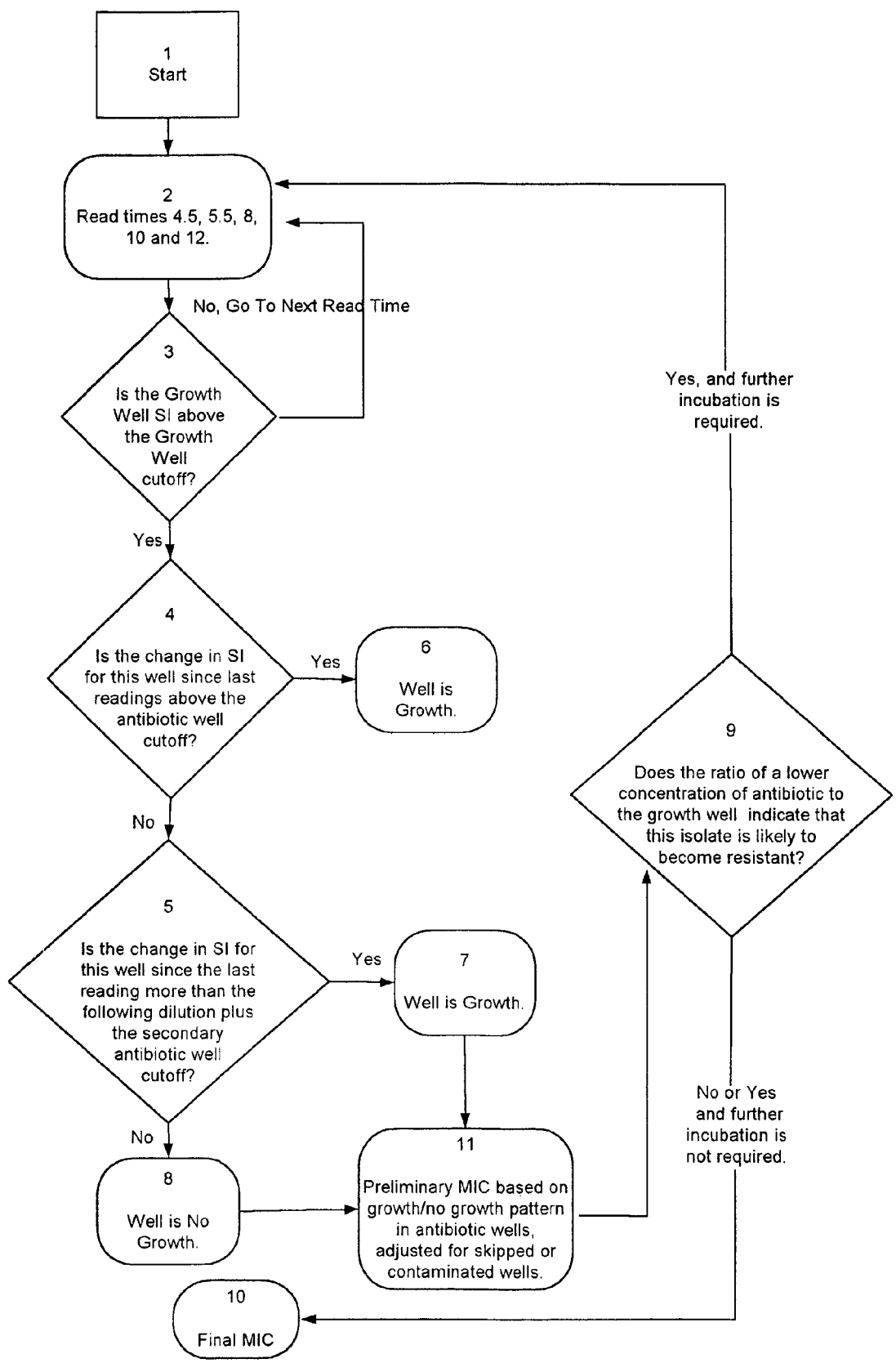
FIG. 1 illustrates a new algorithm useful for AST determinations in accordance with the teachings of the present invention.

As noted above, the present invention discloses methods of determining antimicrobial susceptibility and confirming the identity of a variety of microorganisms using methods that are readily and easily adapted for use in automated assays. The within-disclosed methods differ from those in the art in at least four important respects: (1) the use of a hybrid panel, in which samples are assayed via fluorescent as well as turbidimetric assays; (2) use of a modified, clear plastic panel for the simultaneous (or independent) assay of samples via fluorescent identification (ID) and/or turbidimetric antimicrobial susceptibility testing (AST); (3) the use of multiple wavelength optics (e.g. bichromatic analysis) to enhance assay sensitivity and accuracy; and (4) the use of novel methods, including formulas and algorithms, to determine incubation time and susceptibility results. These aspects of the invention, as well as others, are described in greater detail below.

Before addressing the novel aspects of the present invention, however, it may be helpful to provide an overview of an exemplary automated assay system—namely, the WALKAWAY® system available from Dade MicroScan Inc. (West Sacramento, Calif.). It should be understood that the methods, compositions, and constructs of the invention may readily be adapted to other systems, however, including other commercially-available automated assay systems.

A. Overview of an Automated Assay System

1. Instrumentation Overview

The WALKAWAY® system is an automatic specimen analyzing system that substantially reduces operator involvement over other presently-available systems. After the operator loads the specimen trays into the system of this invention, various operations including incubation after inoculation, adding reagents and analysis of the specimen following incubation are all handled automatically without further operator involvement. A computer-type processor controls the system so that the various operations are carried out in appropriate sequence and the results of the analysis are recorded with specific reference to the sample analyzed.

Typically, the specimens are arranged in a plurality of specimen trays wherein each of the trays is adapted to contain a plurality of specimens. The system includes one or more tray towers for supporting a plurality of the specimen trays. A work station is located adjacent to the tray tower for selectively treating and analyzing the specimens. Selectively operable tray moving devices associated with the work station are arranged to remove the tray from the tray tower and move it to the work station or to reinsert the tray in the tray tower after the operations at the work station have been completed.

Automated systems for processing a biologic specimen to which fluid must be added generally include a fluid dispensing work station within a housing as well. The system includes a work station having a source of fluid that is to be added to the specimen during processing. The work station includes a fluid dispensing area and a nozzle for dispensing the fluid.

Multimodal carrier mechanisms may also be included. For example, the carrier mechanism can operate in a first mode for movement in the work station during fluid dispensing operations. The carrier mechanism can also operate in a second mode for movement outside the work station to do another processing function not involving the work station. A controller mechanism selectively switches the mode of operation of the carrier mechanism between modes.

The system may further include a docking mechanism that couples the nozzle to the carrier when it operates in its first mode to help dispense fluid. The docking mechanism releases the nozzle from the carrier when it operates in its second mode, freeing the carrier to do other processing functions out of association with the nozzle.

The system may optionally include a second work station for performing a second processing function on the specimen. Additional work stations may be provided when and as needed.

For additional details regarding the WALKAWAY® system and components thereof, see, e.g., U.S. Pat. Nos. 5,888,760, 5,645,800, 5,518,686, 4,676,951, 4,643,879, 4,681,741 and 4,448,534, the disclosures of which are incorporated by reference herein.

2. Assay Capabilities

The WALKAWAY® system has the ability to identify microorganisms belonging to any one of widely divergent groups of microorganisms using biochemical test batteries appropriate for the general microbial sub-class (i.e.: Gram negative or Gram positive), each having a specific formulation (see, e.g., U.S. Pat. No. 5,888,760, the disclosure of which is incorporated by reference herein.) This format provides biochemical identification systems that produce identification results in as short an incubation time as 15 minutes, or up to 8 hours (a single work shift). The tests may be chromogenic/colorimetric, or fluorogenic/fluorometric in nature, and may be read visually or automatically. A database (probability matrix) used to classify and identify the microorganisms comprises either a single database having members of all sub-classes to be identified, or series of sub-databases which are specific to each family within a sub-class. This probability matrix is sometimes referred to hereinafter as a predetermined standard.

One advantage of the WALKAWAY® system to the user is that the user need only learn how to use a single test methodology for the majority of their microorganism identification needs. The general methods associated with isolation, inoculum preparation, assay inoculation, incubation, and test result reading are essentially identical for each biochemical test battery selected. As noted previously, biochemical test batteries (identification [ID] assays) may be run separately, or they may be run concurrently or in combination with AST assays.

With respect to ID assays, classification of a particular microorganism in one of these widely divergent groups is largely based on the growth requirements for those particular microorganisms. For example, staphylococci, streptococci and enterococci have similar growth requirements as do enterics and nonfermenters. In the past, divergent groups of microorganisms have been detected by observing growth on well-known biochemical formulations specifically tailored to each family or group (e.g., growth media specific for yeast, anaerobic bacteria, or fastidious bacteria, etc.).

Examples of these widely divergent groups or families of microorganisms comprise (i) yeast and anaerobic bacteria; (ii) yeasts and *Staphylococcus* sp., *Streptococcus* sp., and/or *Enterococcus* sp.; (III) yeasts and enteric bacteria; (iv) yeasts, anaerobic bacteria, and fastidious bacteria; (v) fastidious bacteria and yeast; and (vi) anaerobic bacteria and fastidious bacteria. Examples of non-divergent groups or families of microorganisms comprise, e.g., (i) enteric bacteria and non-fermenters; (ii) *Staphylococcus* sp., *Streptococcus* sp., and/or *Enterococcus* sp.; and (iii) *Neisseria* and *Haemophilus*. Examples of microorganisms belonging to the foregoing groups can be found in the art; see, e.g., U.S. Pat. No. 5,888,760 (esp. Tables II-V).

The assay systems of the present invention are capable of subjecting a sample to a predetermined biochemical test battery appropriate for the microbial sub-class to facilitate the detection of at least one enzyme and/or groups of enzymes in a metabolic pathway, unique to a microorganism family, genus and/or species in order to identify the microorganism. A biochemical battery is sometimes referred to hereinafter as a combination of tests or a test system. The term "sample" as used herein generally includes a microorganism suspension derived from a colony grown on selective or non-selective media-most preferably a suspension of a substantially pure culture. The term "microbial sub-class" generally refers to either Gram negative or Gram positive microorganisms.

The test systems of the present invention include a plurality of reaction chambers for performing the biochemical tests, wherein each reaction chamber is disposed to receive or contain one or more assay reagents. For example, an assay reagent may comprise a substrate for at least one enzyme, wherein the substrate if acted on by the enzyme(s) results in formation of a detectable product in the reaction chamber and wherein the detectable products in the combination of tests are related to the identity of a microorganism in a sample. Reagents may be dispensed into the panel before or during the operation of the system. The various reagents may conveniently be provided in liquid or dried (e.g. lyophilized) form.

In preferred embodiments, the reaction chambers are disposed in a single housing, e.g., a microtiter tray, herein referred to as a "panel." The number of reaction chambers in the panel can vary depending upon the particular application. The reaction chambers are open or covered, as desired.

Using a MICROSCAN® panel as an example, the reaction chambers (or wells) are typically arranged in a rectangular configuration in an array of 12 wells across and 8 wells down, for a total of 96 wells. (It should be understood that the panels of the present invention are not limited to this configuration; this is, however, a useful configuration.)

Panels generally include a growth well and a control well. The growth well contains growth media for the determination of whether a particular organism can grow in the panel. The well also shows that the panel has been inoculated. A panel is not read if there is no growth in the growth well. The control well is not inoculated and will show growth only if the panel is contaminated. A panel is not read if there is growth in the control well. The readings from the control well in rapid fluorogenic panels is also used in the minimum inhibitory concentration (MIC) algorithms. And as noted previously, the remainder of the wells may contain biochemicals only, antimicrobials only, or both biochemicals and antimicrobials, for rapid and convenient determination of AST and/or ID data.

The test systems of the invention comprise at least one panel having disposed therein a plurality of reaction chambers, e.g., wells, containing a substrate for at least one enzyme and other components for the test. A combination of predetermined biochemical tests appropriate for the microbial sub-class may be performed using a test panel containing 48-96 reaction chambers, although there is no absolute minimum or maximum number of chambers required. The wells are preferably disposed in linear arrays on the test panel to facilitate use of preferred semi- or fully automated sampling, visualization, and data handling methods.

Generally, a battery of biochemical tests suitable for use in the test systems of the present invention are selected by using known statistical techniques to identify a battery of tests capable of identifying desired multiple families of microorganisms within each microbial sub-class. Different databases are then constructed, and those different sets of databases are then evaluated using well known statistical techniques (see, e.g., U.S. Pat. No. 5,888,760, the disclosure of which is incorporated by reference herein). The database (e.g. probability matrix) or predetermined standard used to identify the microorganisms comprises either a single database comprising members of all groups to be identified, or a series of sub-databases which are specific to each microbial sub-class. As previously mentioned, major advantages of this system to the user is that they need only to learn how to use a single test methodology for the majority of their microorganism identification needs.

In general, the single database or series of sub-databases (i.e. the probability matrix) is used as the predetermined standard against which results of the test systems (panels) of a sample are compared to identify the microorganism. Preferably, the predetermined standard is generated from data obtained using spectroscopic or fluorescent (e.g. fluorometric) techniques. However, the predetermined standard can be developed using data, obtained by visual inspection as well—e.g., visual inspection of colorimetric test results. A variety of biochemical tests for the identification of microbial enzymes are known in the art. Most such tests can be adapted for use in test systems such as those disclosed herein.

The test systems of the present invention comprise fluorescence-based tests, or colorimetric-based tests (including turbidimetric tests), or some combination thereof. For example, because of greater sensitivity and speed, fluorescence based tests are preferred for some tests over colorimetric (chromogenic) based tests in the test system of the present invention. However, in other tests in the test systems, colorimetric based tests are preferred because of greater convenience such as visual test interpretation.

Preferably, the test systems of the present invention are capable of identifying a microorganism from multiple groups of microorganisms by using one of two batteries of predetermined biochemical tests; wherein the majority of tests are in a fluorescence based format. In this embodiment, the presence of enzymes and/or groups of enzymes in a pathway are detected by determining the presence of detectable fluorescent products. In some instances, formation of the fluorescent products is a result of a pH change caused by reaction of the enzyme with a substrate (fluorometric test). In other instances, formation of the fluorescent products accompanies cleavage of fluorogenic substrates (e.g., by hydrolysis) to form detectable derivative fluorophores usually exhibiting increased fluorescence (fluorogenic test). In yet other instances, chromogenic products are formed which quenche fluorescent indicators.

Results from the battery of predetermined tests are subjected to various statistical methodologies for the purpose of identifying the microorganism in the sample, i.e., compared to at least one predetermined standard.

The test systems of the present invention are conveniently configured as panels having a predetermined number of reaction chambers or wells. Such configurations will be used to illustrate the test systems of the present invention. This is not intended to be limiting of the test systems; they can be configured in a wide variety of suitable formats to meet the intended use.

The panels referred to herein are capable of identifying a microorganism in a sample from one of multiple and widely divergent groups of microorganisms. For example, a panel of the present invention generally comprises a predetermined battery of non-redundant biochemical tests disposed in a predetermined number of reaction chambers; for convenience of storage and use, the panels are preferably in dried form. Each panel has been specifically configured to contain biochemical tests most appropriate for the microbial sub-class to be identified. The reaction chambers or wells in the panels may thus be rehydrated upon use in conjunction with the apparatus and systems of the present invention.

Each biochemical test in the panels comprises a substrate for an enzyme or a group of enzymes. When a substrate is acted on the enzyme or group of enzymes forms detectable products in the reaction chamber, and the detectable products from the combination of tests are used to identify the microorganism(s) in the sample.

The term "non-redundant," as used herein in connection with the test system of the present invention is meant to indicate that a substrate is not used more than once in a panel. However, in some instances it may be desirable to include the same substrate a number of times—e.g., in a different buffer system.

B. Hybrid Panels and Related Devices

A new approach to obtaining rapid AST results, described in greater detail hereinbelow, utilizes turbidimetric measurement of growth rather than depending solely on indirect fluorescent measurement. This approach is based on the surprising observation that our spectrophotometric instruments can detect between 1 to $2\times10^7$ cells/mL which is the same approximate cell number that indirect fluorescent measurements detect. Therefore, the sensitivity between the two methods is roughly equivalent when using the same initial inoculum of $5\times10^5$ bacterial/mL.

As a result, we have now found that rapid turbidimetric measurements can be used for rapid AST using existing media formulations. Moreover, using turbidimetric data, an incubation time can be assigned for instances in which an accurate MIC can be determined in a very short period of time (e.g. ≤8 hours) in addition to being able to be used to determine MICs over a longer time period, having the ability to hold and read panels incrementally up to 24 hours. Therefore, the combined use of fluorescent ID and turbidimetric AST generates same-day results for a significant majority of isolates. The use of multiple wavelength optics in turbidimetric assays is also novel and thus the assays and systems of the present invention provide a more accurate read as well as a more prompt and reliable one.

The fluorescent identification (ID) of the present "hybrid" assay system—as well as the AST assay—uses a unique clear plastic panel. (The terms "sample-containing device" or "tray" may also be used interchangeably with "panel.") The fluorescent ID is, however, determined in a very similar fashion to the existing fluorescent ID read on white panels—i.e. fluorescence from each well is determined at several read times, and based on the rate the fluorescence increases, the test is scored either as positive or negative. In an exemplary system—e.g. the WALKAWAY® system (Dade MicroScan Inc., West Sacramento, Calif.), the panel is inoculated essentially identically to the manner in which existing fluorescent rapid combination ("combo") panels are inoculated.

The present invention is ideal for use with panels that are not "combo" panels, but it is especially useful with "combo" panels which preferably include both biochemicals and antimicrobials for use in ID and MIC testing—hence the term "combo." For example, Dade MicroScan Inc. provides panels identified as "ID/MIC Combo" panels, which include both biochemicals and microbials for the determination of the test organism's identity and MIC. Panels conveniently identified as "Breakpoint Combo" panels are also available and include biochemicals and antimicrobials in one or two specific dilutions. If two dilutions are present, they are preferably on either side of the established susceptibility level or "Breakpoint" (BP).

The hybrid panels disclosed herein use clear plastic for both the ID and MIC which makes manual scoring of 16 hour AST results possible when needed. While it is generally not feasible to manually read the fluorescent ID at 16 hours, the fluorescent ID may be readily determined at least a dozen hours earlier using appropriate instrumentation.

The fluorescent ID is generally inoculated with a 0.5 McFarland ($1\times10^8$ bacteria/mL) inoculum for 2-2.5 hour identifications, and may be inoculated with less-concentrated inoculums, i.e. $2.5\times10^7$ for 3-3.5 hours. In general, the susceptibility portion of the panel is inoculated with a 1 to 250 dilution of the 0.5 McFarland inoculum (i.e. $4\times10^5$ bacteria/mL), or is inoculated with a PROMPT® inoculation wand (3M, St. Paul, Minn.). Further details regarding assay procedures are provided in the Examples below.

The susceptibility portion of the panel is read turbidimetrically using the colorimeter of an appropriate automated assay device (e.g. the WALKAWAY®) using at least two, and often three, distinct wavelengths of light—e.g. 405, 505 and 620 nanometers (nm)—at the following times: 2.5 hours, 4 hours, 6 hours, 8 hours, 12 hours, 16 hours, and 24 hours after the fluorescent ID has been determined. The times and wavelengths described herein are exemplary and not limiting, however. The read times and/or the number and type of wavelength used may readily be adjusted to enhance the accuracy and rapidity of the determinations.

As noted above, another important aspect of the hybrid assay system is the use of clear plastic specimen trays or panels. White plastic materials have traditionally been used in the manufacture of fluorescent panels in order to avoid a phenomenon known as fluorescent cross-talk (or crossover) from well to well. Colored plastic trays with clear plastic bottoms have also been proposed for use, but they are much more expensive to manufacture than are clear plastic trays and they do not readily lend themselves for use in turbidimetric/colorimetric assays (i.e. optical assays) as well as in fluorogenic assays, unlike the modified clear plastic trays/panels of the present invention. The use of the clear panels of the present invention allows one to run AST and ID assays using a single panel, thereby saving time and reducing the need for operator involvement.

Fluorescent crossover is defined as the percent fluorescence of the total signal in a test well that results from fluorescence in adjacent wells. White plastic exhibits no fluorescent crossover whereas clear plastic, under circumstances other than those disclosed herein, has significant crossover that can alter interpretation of the ID. That is, low test well fluorescence adjacent to wells with high fluorescence may also appear high, thus producing a false positive reading.

When designing the new clear plastic panels, it was observed that fluorescent cross-talk occurred between wells within the same row on the panel but did not occur between wells within the same column on a panel. From this and other observations, it was determined that two factors influence the amount of cross-talk. The first factor is the width of the read frame of the fluorometer, i.e. the physical distance along the row axis that the fluorometer excites and collects light from a single well. Often, the read frame used in systems reading fluorescent ID results is too broad, so that light from adjacent wells on the same row contributes to the fluorescent signal of the primary well (the well being read at the moment). This signal-contamination phenomenon is generally referred to as "cross-talk."

Therefore, in addition to improving assay performance and accuracy via the development of a hybrid assay system, another aspect of the present invention emphasizes the development of an ID product on clear plastic that has the same accuracy as a product on white plastic. This has been accomplished via our use of two approaches that have been demonstrated to substantially reduce cross-talk individually and to block it 99% or more when used in combination.

The first approach involves the reduction or narrowing of the read frame. Narrowing the fluorometer read frame reduces the amount of cross-talk substantially. Optimization of the read frame/read window result in the blocking of at least 90% of cross-talk.

The second factor that contributes to cross-talk is based on the optic properties of the plastic itself. In general, the orientation of the grain of the plastic comprising each well is different from the grain of the plastic on the top surface of the panel. The well plastic acts as a light pipe, creating a halo of light around each well when each well is excited with light. However, when the top surface has been modified near the lumen of the test well with a surface that blocks the light pipe effect, cross-talk is substantially suppressed. For example, material such as, but not limited to ink, dyes and paint may be used to provide the clear plastic plate's top surface with an opaque surface. One particularly useful method of providing the plate with an opaque surface is pad printing a solid color of black, blue, or red around each well, without modifying the well itself.

Thus, a second solution to the crossover problem, i.e. modification of the surface of the plastic, also reduces cross-talk. Application of the second solution—modification of the surface of the plastic—produces a blockage of at least 90% of cross-talk, as does application of the first solution alone. Thus, the use of both approaches simultaneously allowed us to achieve a 99% or greater blockage of cross-talk.

Once the problems associated with cross-talk had been resolved it was noted that the Artificial Florescent Units (AFU) generated using clear plastic were significantly less than when white plastic trays were used. By way of background, and not intended as limitation, AFUs are generated in one embodiment of the present invention when a light energy source of wavelength between approximately 250 nm and approximately 420 nm, preferably 370 nm, is directed into a well containing a free fluorochrome. The free fluorochrome is excited by the 370 nm light energy and emits a light energy at approximately 450 nm in response. The more free fluorochrome present in the sample (which is directly proportional to the amount of microbial growth and/or enzyme activity) the more 450 nm light energy that is emitted. The 450 nm light energy emitted by the fluorochromes of the present invention are detected by a photomultiplier tube, or voltage count oscillator (VCO), that converts the light energy to voltage. The voltage emanating from the VCO is converted into an AFU by an onboard microprocessor using imbedded software.

However, a significant amount of light energy is lost when clear plastic trays are used resulting in diminished voltage from the VCO, consequently AFUs calculated by the onboard computers are much lower than when white plastic trays are used. This in turn results in values that do not correlate with the extensive database complied testing organisms using white plastic plates. As a result, the AFUs generated using clear plastic do not provide meaningful results. This lack of linearity between the clear plastic and white plastic is corrected by using a mathematical function. Consequently, the AFUs generated using the clear plastic plates of the present invention can be used with the existing data bases without requiring extensive re-testing and system re-validation.

It should also be appreciated that the clear plastic panels (or trays) of the present invention lend themselves for use in non-combined or non-hybrid assay contexts. For example, the modified clear plastic panels of the invention are useful in the conduct of AST or MIC testing only, or in the conduct of ID testing only. That is, the invention is not limited to use of the novel plastic trays in hybrid combination AST/ID testing alone.

C. Incubation Time Methods and Algorithms

Minimum inhibitory concentration and BP values are determined by comparing the test wells (wells containing the anti-microbial) with the growth control well (a well of anti-microbial-free nutrient medium that is inoculated with the sample). growth/no-growth determinations comparing the test wells and growth control well are done at predetermined intervals according to the algorithm of the present invention. A Susceptibility Index (SI) is calculated for each test well and growth control well as follows. A first turbidity reading is taken for each test well (Di) and control well (Ci) and the absorbance data is stored. Next, at a predetermined interval, a second turbidity reading is taken for each test well (Df) and control well (Cf). A ratio of (Df−Cf)/(Di−Ci) is calculated resulting in an SI. If the ratio is greater than one, growth has occurred and the test can be read. If the ratio is one, then no growth has occurred and the WALKAWAY; system using the smart algorithm (FIG. 1) of the present invention will automatically hold the samples and re-read them at the next scheduled interval.

For example, after a turbidity read has occurred, the raw data is processed on board the assay system. At the 6 hour read, data from the 2.5 and 4 hour reads is used to determine if a Break Point (BP) or a Minimal Inhibitory Concentration (MIC) can be accomplished/determined or if further incubation is required. (This depends on whether a BP panel is used to determine the BP or a MIC panel is used to determine a MIC, respectively.) As noted previously, the term AST testing generally encompasses both BP and MIC testing—although it should be appreciated that one may conduct one or the other test method where appropriate.

If it is not possible to determine either a BP or MIC at 6 hours, then the panel is incubated for an additional two hours. At 8 hours, data from the 2.5 and 6 hour reads is used again to determine either a BP or MIC or if further incubation is required. If it is not possible to determine either a BP or MIC at 8 hours, the process is repeated to 12, 16, or 24 hours. At each time point, specific questions are asked of the raw data in the related software (e.g. MICROSCAN® Data Management System software, Dade MicroScan Inc., West Sacramento, Calif.) to determine if further incubation is required or whether the susceptibility results can be reported.

The algorithm of the present invention is unusual in several aspects. First, it is a "smart" algorithm in that it interacts in an intelligent manner with the overall assay system to determine appropriate incubation times for the samples and sample/reagent admixtures in order to produce an accurate, reliable reading. In most instances, the algorithm may be applied to enhance analysis of the information gathered from the specimens so that results are obtained more quickly than in the past. However, unlike previously-used algorithms, the "smart" algorithm of the present invention does not sacrifice accuracy for speed. For example, when the algorithm determines that a longer incubation time is necessary for a particular specimen, it can override the MIC to ensure an accurate result.

Using the WALKAWAY® system as an example, the WALKAWAY® can be simply described as comprising 3 main physical components: (1) hardware; (2) firmware; and (3) "externals." The term "firmware" is intended to refer to on-board computer system(s) that run the WALKAWAY® instrument, while "externals" is intended to refer to the computer system(s) that is not physically incorporated into the WALKAWAY® system. "Hardware" thus identifies the other physical components, such as the dispensers, optics, trays, etc.

Thus, in this context, it is possible to make the smart algorithm a resident of the "firmware" or the "externals." While the examples herein recite that the algorithm is included in software resident in the "firmware" of the WALKAWAY® system, it should be appreciated that the algorithm may alternatively be included in software resident in the "externals," or in both locations. Since the "firmware" and the "externals" are readily able to communicate with each other, the physical location of the protocols that run the automated assay system need not be relegated solely to one site or the other.

In addition to the smart algorithm, other higher levels of information are also useful in the determination of incubation time. These levels of information include the following:

1. Based on either the ID obtained from the fluorescent ID or from presumptive ID information, it can be determined from National Committee for Clinical Laboratory Standards (NCCLS) guidelines whether the delayed drug is useful as a therapeutic choice. If the delayed incubation antibiotic is not useful therapeutically, the algorithm would not report it and would release susceptibilities on all other drugs on the panel.
2. The values from other drugs from the same class or similar mechanisms of action can potentially be used to assess whether an early read is valid or whether further incubation is required, i.e. ampicillin or mezlocillin indicate activity of pipercillin.
3. When a "combo" panel is used, an algorithm is used to determine if a mixed inoculum has potentially been added based on the likelihood score. The likelihood score determines how many tests are different from the probability matrix value. The lower the value the fewer the tests that match. In general, IDs with likelihood values of $10^{-8}$ or lower are further incubated. Extremely low likelihood values suggest more than one species of microorganism may have been present in the inoculum (a mixed culture). When the inoculum contains a mixed culture, the ID and AST results are invalid. To ascertain if a mixed culture was used a purity check plate is inoculated and analyzed. If the purity check plate indicates that more than one microorganism was present in the original inoculum the results are deemed invalid and the sample is reset using a pure culture D. Elimination of False Susceptible MICs A new feature is available for beta lactams and cephalosporins to help prolong the incubation time applying to isolates that might otherwise generate false negatives. It was observed that when examining patterns of a broad range of gram negative microorganisms, a correlation exists between the amount of growth (the absolute SI of the growth well), at the SI of sub-inhibitory concentrations of antibiotic, and the ceiling of false susceptible MICS when performing rapid-time-to-detection ASTS.

This correlation can be determined by calculating the ratio of the growth well SI to the ratio of the drug well SI. That is, if an organism is truly resistant to an antibiotic, the ratio of growth SI to sub-inhibitory SI is close to 1. For organisms that are truly susceptible, the ratio is generally very large, approaching infinity. However, for organisms that have delayed responses to an antibiotic, and therefore can result in false susceptible calls, the ratios fall in-between—e.g. they have values of, for example, 1.5, 2, 3, and the like.

By looking at the concentration of antibiotic which results in full inhibition, at a sub-inhibitory concentration with a ratio greater than an as-yet-to-be-determined value (i.e. greater than 1 but less than infinity) and at the growth SI with values above an as-yet-to-be-determined threshold, those organisms which are called false susceptible can be differentiated from true susceptible organisms. That is, when all of the above conditions are evaluated and used to create a data pattern, a distinct sub-population within this pattern emerges. By using the algorithm to have the instrument incubate this distinct sub-population longer than the other population of isolates, a more accurate susceptibility result is obtained.

The basis of this unique sub-population is based on firm microbiologic mechanisms. That is, some microorganisms have lower activity beta lactamases. These lower-activity isolates may occur because the specific activity of the enzyme is lower or because the number of enzyme molecules present is low, e.g., inducible beta lactamases. In the presence of sub-inhibitory concentrations of antibiotic, it takes more time to reduce the initial concentration of antibiotic to a level that allows maximal growth. From the evaluation of sub-populations of isolates tested during database development, it appears that isolates with lower activity (i.e. beta lactamase activity) can be differentiated from higher activity isolates which can be used to increase incubation time and therefore accuracy of the final result.

Application of the algorithm shown in FIG. 1 takes advantage of the observation that the change in SI drug/delta SI growth well ratio is a significantly better indicator than previously-used methods. As a result, the predictive capability of any assay conducted as described herein is without peer.

Additionally, multiple time reads for each drug dilution (test well) using monochromatic light can be used to augment the algorithm/SI ratio method for identifying false susceptible microorganisms. Briefly, monochromatic light is used to read optical density (also known as processed value or PV in the present invention) in each test well at a predetermined interval (T1). If this initial PV (PVx) is less than a predetermined minimum value established to indicate growth (growth threshold), it is retained for comparison to a second PV (PVy) obtained at a later time (T2). If PVy remains below the growth threshold, it is compared to PVx and to the PV obtained at T2 for the next highest concentration of drug (PVz). If PVy is greater than PVx and PVz then growth is considered to have occurred in the test well and the microorganism is considered resistant to the drug at the test well concentration.

E. BP or MIC Determination Using Multiple Wavelength Optical Analysis

After incubation, either a BP or a MIC determination is carried out. The overall algorithm concept is very straightforward. If growth occurs in a well, then the organism is resistant to that level of antibiotic. If no growth is detected, the organism is susceptible to that level of antibiotic.

However, many factors can influence the determination of whether growth has occurred in a specific well, including instrument drift, variation in plastic, media variance (including lot to lot variance of subcomponents), and other such factors. Further, instrument sensitivity, i.e. the lowest number of bacteria the instrument can detect, also is critical for determination of growth.

The existing colorimeter in many automated systems uses a wavelength of 620 nm to determine turbidity. Even with multiple reads, use of a single wavelength may not provide sufficient information. To improve the sensitivity of our devices and systems, the colorimeter uses a minimum of two of the following three wavelengths—i.e. 405, 505, and 620 nm. As the most sensitive turbidimetric measurements appear to occur at 405, this system is designed to have improved sensitivity and therefore enhanced accuracy in the performance and interpretation of assay results.

To develop the most sensitive noise-free signal, an approach called bichromatic analysis is used to determine growth. Essentially, this process optimizes the signal to noise ratio in each well. What follows is a description of this approach for determining growth.

The monochromatic method of spectral analysis involves selecting a single wavelength that contains a unique spectral feature for the analyte of interest. In the conventional method, the analyte is turbidity and its measurement at 620 nm wavelength is used to quantify growth.

The precision of photometric measurements at the 620 nm wavelength is limited by various factors, including the following. First, sensitivity is low, as there is a growth curve with small curve size. Second, there are photometer-dependent spectral variations: variation from the diffuser plate, interference filters, and fiber optics. Third, panel-dependent spectral variations are not uncommon, and include variation from the optical path length of wells, the well to well difference within a panel, variation from panel position, well cleanliness, well plastic material, and well concave-bottom shape. Finally, there are chemical-dependent variations, including variation from broth to broth, and the presence of foreign material not related to growth.

These factors add several layers of noise to the single-wavelength photometric measurement but all should be removed when multiple wavelength optics are used because when two or more wavelengths are used, they are affected equally at the signal measurement station. For the purpose of providing a non-limiting example, bichromatic photometry will be discussed briefly as an example of multiple wavelength optics useful according to the present invention.

In bichromatic photometry, two wavelengths are selected for use: a primary wavelength and a secondary one. In assays utilizing a chromogen, the primary wavelength is near the absorption peak of the chromogen being analyzed. The secondary wavelength is carefully selected off to the side of this peak where there is a minimum change of absorbance. If no chromogen is being added—e.g. when turbidimetric readings are being taken—the selection of primary and secondary (and tertiary, etc.) wavelengths is made as set out below.

Figure 2:
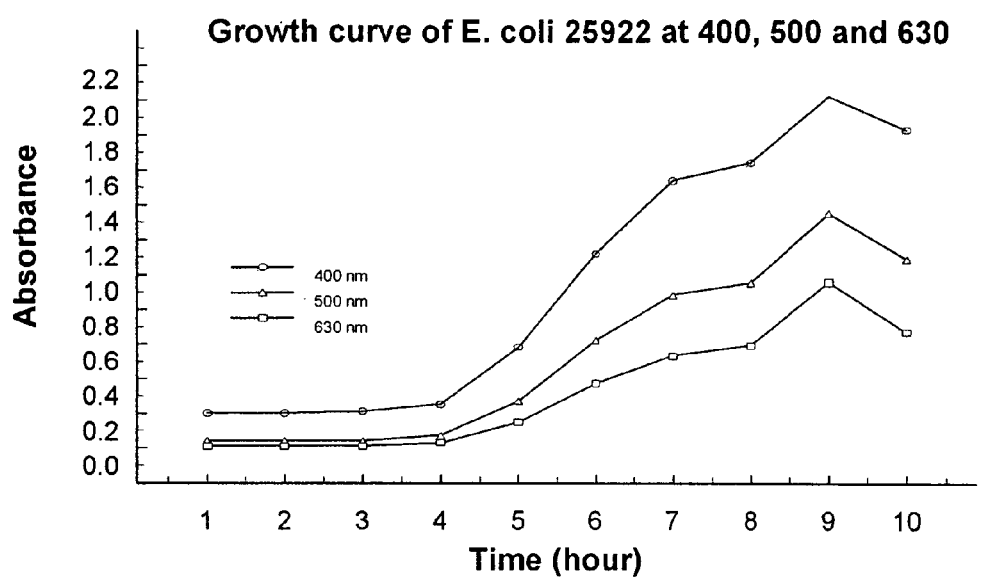
FIG. 2 illustrates the growth curve of *E. coli* 25922 in gram negative broth at three different wavelengths in accordance with the teachings of the present invention.

FIG. 2 shows the growth curve of *E. coli* 25922 in Gram negative broth at three different wavelengths. The turbidity spectrum shows a band with no absorption peak but higher absorbance at lower wavelength. In the instrument, the available wavelengths are 405, 440, 505, 560, 590, and 620 nm. Since turbidity is low at higher wavelengths, the secondary wavelength should be 620 nm because growth is the lowest among the available wavelengths. This is not an ideal secondary wavelength because growth does occur at this wavelength. However, if the final growth is measured early (between 4 and 6 hours and sometimes 8 to 10 hours), the changing absorbance at 620 nm should have a minimal effect on the bichromatic measurement.

The primary wavelength can be any wavelength below 620 nm provided that the initial absorbance of the broth from the drug well and the final absorbance are within the dynamic range of the photometer.

For Gram negative organisms, the sensitivity significantly increases at 405-620 wavelengths due to the increased curve size for most drugs except tetracycline and Nitrofurantoin. The broth for these drugs is yellow to light brown and absorbs strongly at lower wavelengths. The 505-620 wavelengths appear to work better for tetracycline and Nitrofurantoin than other bichromatic wavelengths. For Gram positive organisms, the 505-620 wavelengths were selected because Gram positive broth has a dark brown color and its initial absorbance is high at lower wavelengths.

Examples showing the improvement in assay sensitivity are illustrated in the following comparative Tables.

TABLE 1

CONVENTIONAL METHOD USING ABSORBANCE AT 620 nm
Organism: *C. freundii* 104 manual read MIC 2 µg/mL
Drug: Tobramycin

| Drug Level | Time | | | | | MIC |
|---|---|---|---|---|---|---|
| µg/mL | 4 hrs | 16 hrs | Processed Value | Breakpoint | Growth | µg/mL |
| 0.5 | 1891 | −2425 | 1891 − (2425) = 4316 | 400 | G | |
| 1 | 2300 | 287 | 2300 − 287 = 2013 | 400 | G | |

TABLE 1-continued

CONVENTIONAL METHOD USING ABSORBANCE AT 620 nm
Organism: *C. freundii* 104 manual read MIC 2 µg/mL
Drug: Tobramycin

| Drug Level | Time | | Processed Value | Breakpoint | Growth | MIC |
|---|---|---|---|---|---|---|
| µg/mL | 4 hrs | 16 hrs | | | | µg/mL |
| 2 | 2553 | 2859 | 2553 − 2859 = −306 | 400 | N | 2 |
| 4 | 2723 | 3036 | 2723 − 3036 = −313 | 400 | N | |
| 8 | 620 | 2891 | 620 − 2891 = −2271 | 400 | N | |

TABLE 2

NEW AST METHOD USING BICHROMATIC ABSORBANCE
BETWEEN 405 AND 620 NM WAVELENGTHS
Organism: *C. freundii* 104 manual read MIC 2 µg/mL
Drug: Tobramycin

| Drug Level | Raw absorbance at 620 nm | | Raw absorbance at 620 nm | | Preprocessed Bichromatic Absorbance at 620-405 nm | |
|---|---|---|---|---|---|---|
| µg/mL | 3 hrs | 6 hrs | 3 hrs | 16 hrs | 3 hrs | 6 hrs |
| 0.5 | 1891 | −1516 | 773 | −4996 | 1891 − 773 = 1118 | −1516 − (−4996) = 3480 |
| 1 | 2300 | 1706 | 1186 | 12 | 2300 − 1186 = 1114 | 1706 − 24 = 1682 |
| 2 | 2553 | 2795 | 1460 | 1866 | 2553 − 1460 = 1093 | 2795 − 1866 = 929 |
| 4 | 2723 | 2970 | 1674 | 2090 | 2723 − 1674 = 1049 | 2970 − 2090 = 880 |
| 8 | 620 | 2823 | 1418 | 1843 | 2568 − 1418 = 1150 | 2823 − 1843 = 980 |
| Control well | 3334 | 3552 | 3431 | 1768 | 3334 − 3431 = −97 | 3552 − 3768 = −216 |
| Growth well | 3085 | −480 | 1705 | −4571 | 3085 − 1705 = 1380 | −480 − (−4571) = 4091 |

| Drug Level µg/mL | Preprocessed Value $D_6 − C_6$ | Breakpoint $D_3 − C_3$ | Susceptibility Index $(D_6 − C_6)/(D_3 − C_3)$ | MIC µg/mL |
|---|---|---|---|---|
| 0.5 | 3480 − (−216) = 3696 | 1118 − (−97) = 1205 | 3696/1205 = 3.0 | |
| 1 | 1682 − (−216) = 1898 | 1114 − (−97) = 1201 | 1898/1201 = 1.6 | |
| 2 | 929 − (−216) = 1145 | 1093 − (−97) = 1180 | 1145/1180 = 1.0 | 2 |
| 4 | 880 − (−216) = 1096 | 1049 − (−97) = 1136 | 1096/1136 = 1.0 | |
| 8 | 980 − (−216) = 1196 | 1150 − (−97) = 1237 | 1196/1237 = 1.0 | |
| Growth well | 4091 − (−216) = 4307 | 1380 − (−97) = 1467 | 4307/1467 = 2.9 | |

TABLE 3

CONVENTIONAL METHOD USING ABSORBANCE AT 620 nm
Organism: *C. freundii* 87 manual read MIC greater than 256 µg/mL
Drug: Sulfamethozazole

| Drug Level | Time | | Processed Value | Breakpoint | Growth | MIC |
|---|---|---|---|---|---|---|
| µg/mL | 3 hrs | 16 hrs | | | | µg/mL |
| 256 | 1731 | 545 | 1731 − (545) = 1186 | 1800 | N | <256 |

TABLE 4

NEW AST METHOD USING BICHROMATIC ABSORBANCE
BETWEEN 405 AND 620 NM WAVELENGTHS
Organism: *C. freundii* 87 manual read MIC greater than 256 µg/mL
Drug: Sulfamethoxazole

| Drug Level | Raw absorbance at 620 nm | | Raw absorbance at 620 nm | | Preprocessed Bichromatic Absorbance at 620-405 nm | |
|---|---|---|---|---|---|---|
| µg/mL | 3 hrs | 6 hrs | 3 hrs | 16 hrs | 3 hrs | 6 hrs |
| 256 | 1731 | 1255 | 659 | −285 | 1731 − 659 = 1072 | 1255 − (−285) = 1540 |
| Control well | 2087 | 2306 | 2079 | 2405 | 2087 − 2079 = 8 | 2306 − 2405 = −99 |
| Growth well | 1736 | −804 | 414 | −4334 | 1736 − 414 = 1322 | −804 − (−4334) = 3530 |

TABLE 4-continued

NEW AST METHOD USING BICHROMATIC ABSORBANCE
BETWEEN 405 AND 620 NM WAVELENGTHS
Organism: *C. freundii* 87 manual read MIC greater than 256 µg/mL
Drug: Sulfamethoxazole

| Drug Level µg/mL | Preprocessed Value $D_6 - C_6$ | Breakpoint $D_3 - C_3$ | Susceptibility Index $(D_6 - C_6)/(D_3 - C_3)$ | MIC µg/mL |
|---|---|---|---|---|
| 256 | 1540 − (−99) = 1639 | 1072 − (−8) = 1064 | 1639/1064 = 1.5 | >256 |
| Growth well | 3535 − (−99) = 3632 | 1322 − (−8) = 1314 | 3632/1314 = 2.8 | |

F. New AST Method

The current conventional AST method determines growth by comparing the calculated processed value, which is the 620 nm absorbance difference between two (2) hours and forty-five minutes and 16 or 18 hours against a breakpoint. This breakpoint was determined by testing 100-200 isolates and reading results manually or via instruments and correlating the reads of those isolates to their processed values. This approach has limited capability because the processed value is not corrected for system-dependent variations and the breakpoint is not adaptable to system change.

The goals of the new AST method are to achieve higher precision, greater accuracy and increased reliability by using (1) quantitative spectral information derived from bichromatic measurements, (2) a dynamic breakpoint for individual drug wells based on their initial condition, and (3) a susceptibility index for determining susceptibility. The new AST method includes the following processes.

1. Bichromatic Absorbance Calculation at 3, 5, 6, 8, and 10 Hours

Bichromatic absorbance is the difference between the primary wavelength with significant turbidity and the secondary wavelength with little turbidity. For Gram positive organisms, the wavelengths are 505 and 620 for all drugs.

For Gram negative organisms, the wavelengths are 405 and 620 nm for most drugs except Nitrofurantoin and tetracycline. The wavelengths for Nitrofurantoin and tetracycline are 505 and 620 nm.

2. Susceptibility Index (SI) Calculation

The susceptibility index (SI) is the ratio of the initial and final absorbance after correction for system drift. The susceptibility indexes are calculated for each drug well and the growth well (positive control well). The following formula (equation 1) is used to calculate the susceptibility index:

$$\frac{(Df - Cf)}{(Di - Ci)}$$

where

Di=Initial bichromatic absorbance from drug well
Df=Final bichromatic absorbance from drug well
Ci=Initial bichromatic absorbance from control (negative control) well
Cf=Final bichromatic absorbance from control (negative control) well 3. Checking for Sufficient Growth Prior to MIC Calculation Check for growth by comparing the susceptibility index from the growth well to see if it is greater than 1. Theoretically, if there is no growth, the numerator and denominator from equation (1) should be the same and their ratio is 1. It may be necessary later to assign a value to this ratio to safeguard sufficient growth. The susceptibility indices from some slow-growing Gram negative organisms such as *Stenotrophomonas maltophilia* and *Pseudomonas aeruginosa* is between 1.3 and 1.7 at 6 hours from a small set of organisms.

4. Bichromatic Difference to Calculate Growth or No Growth

In addition to an SI (susceptibility index) ratio, a difference value can be calculated—for example, the difference between the initial bichromatic read and the final bichromatic read.

This is based on an existing conventional algorithm approach with the important distinction that bichromatic analysis is used instead of monochromatic 620 nm light. Further, in some instances, the use of an SI and a difference calculation can provide the most accurate determination of growth.

It is also useful to utilize a "delta SI" (i.e., a change in SI) calculation which is essentially described as middle read $SI_{(3.5\,h)}$ minus initial $SI_{(2.3\,h)}$ and final read $SI_{(VARIABLE)}$ minus middle read SI. Again, this can be used with individual SI values, difference values, and delta SI values.

5. Growth/No Growth Determination Using Susceptibility Indices

Compare susceptibility indices from drug wells to determine growth/no growth. A value of 1.05 is presently preferred for use as a cutoff to determine growth. The value may be adjusted as assay procedures undergo further refinement but is nonetheless expected to retain a value approaching 1.

6. MIC Determination

In the current conventional MIC methods used in many art-recognized systems, the MIC is the first no growth well after the last growth well in the dilution series. Difficulties in interpretation occur, however, when there are "no growth" wells interspersed amongst "growth" wells in the same series. Conventional methods treat these no growth wells as "skipped" wells and the MIC is adjusted according to the number of skipped wells. In the methods and systems of the invention, however, an algorithm is applied which more accurately identifies which wells are true skipped wells. In addition, the algorithm is applied to determine which wells are contaminated. Use of the new system increases the accuracy of the read substantially.

7. Longer Incubation Detection

When a drug is applied at sub-inhibitory concentrations during the assays arid methods of the invention, for certain classes of resistance, at one concentration, an organism exhibiting low growth may appear to be susceptible—i.e. the data gathered is consistent with or "tracks" with that of susceptible populations. At another concentration, the test organism may "track" with resistant populations. Thus, methods of determining or detecting when longer incubation periods are required come into play when there is (1) no growth in all wells, or (2) growth in some wells but no growth in other wells, as this pattern is often seen when the test organism is "behaving" as though it were susceptible under certain conditions and resistant under others.

The first situation is difficult to ascertain and may require that an additional dilution less than the current lowest dilution may be needed to detect early growth. In some preliminary trials, it was observed that in only two instances involving the use of locarbef—which is typically assayed using only two dilutions—was it noted that there were no indicators for further incubation at 6 hours.

In the second situation, two conditions must be satisfied before it becomes clear that further incubation may be needed. First, the susceptibility index of the least diluted drug well at six hours must be greater than its susceptibility index at five hours. This condition implies that growth is still taking place. Second, the magnitude of growth in the least diluted drug well has to be small, thereby implying that growth is weak. Preliminary results indicate that this value differs for each organism but tends to be less than 1.7.

Another indicator that further incubation may be required is based on the well-established principle of drug class resistance/susceptibility. For example, if an organism is resistant or susceptible to one drug class member, it is often resistant or susceptible to other drugs within the same class, especially those drugs with similar mechanisms of action. If it would be logical to expect a specific drug class resistance/susceptibility pattern for a given organism based on a preliminary identification, and if results for one drug class member are inconsistent with the expected pattern at 6.5 hours, the plate will be automatically re-incubated and read again at eight hours. At that time the identification will be complete and if the drug class susceptibility pattern is inconsistent with the ID, the AST can be repeated. On the other hand, the extended incubation may reveal that the preliminary ID was incorrect and the susceptibility pattern is consistent with expectations. Finally, the extend incubation may result in an AST interpretation consistent with the confirmed identification.

8. Susceptibility Determination Using Magnitude and Direction of Susceptibility Indices Data from a small set of organisms suggest that an organism is resistant to a drug when susceptibility indices from all drug levels are greater than one and remain constant, intermediate when susceptibility indices are greater than one but decrease with increasing drug levels, and susceptible when susceptibility indices from all drug levels are less than one.

9. Limit of Method: Incomplete Mixing of Broth

Figure 3:
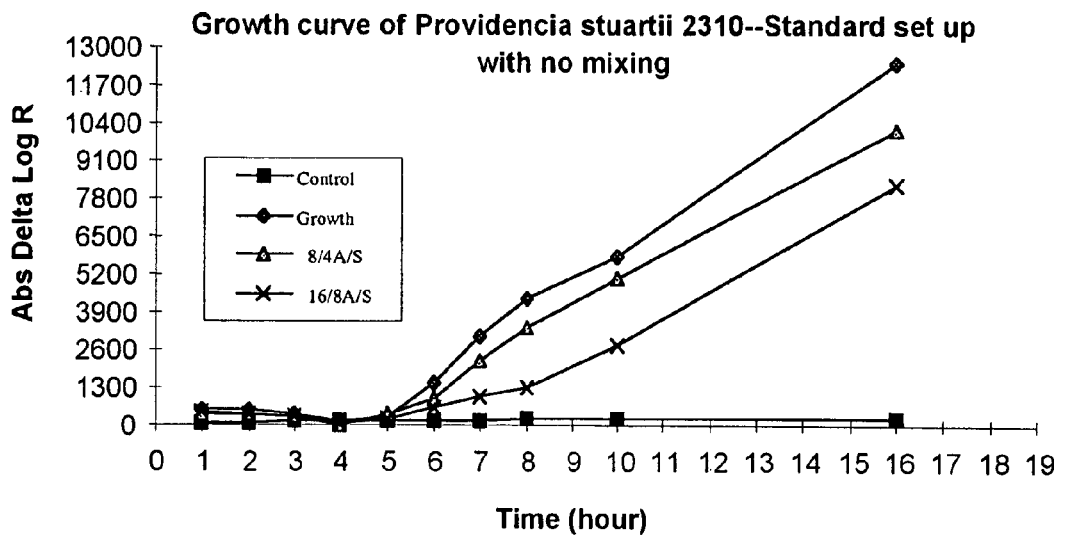
FIG. 3 illustrates growth curves with standard setup—i.e., no mixing of the broth in accordance with the teachings of the present invention.
Figure 3:
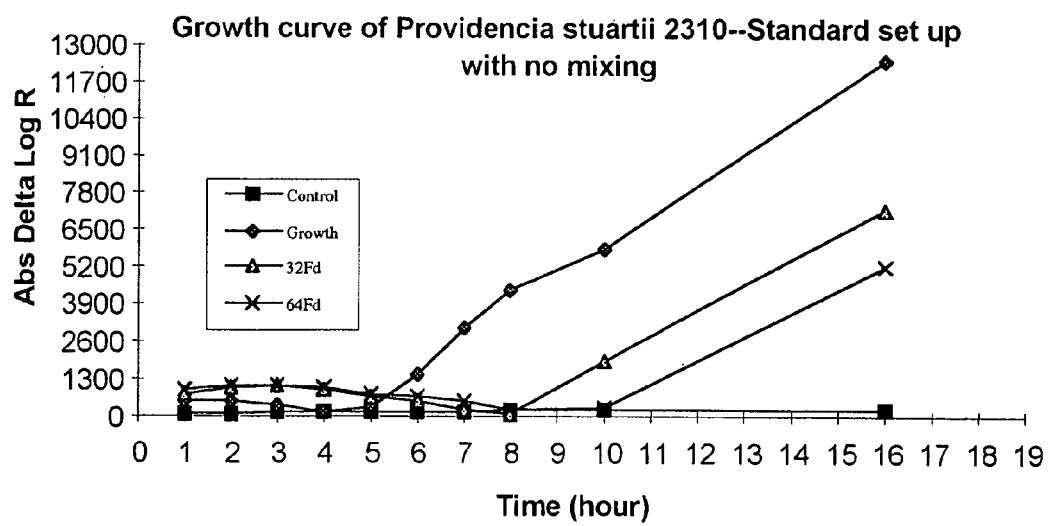
Figure 4:
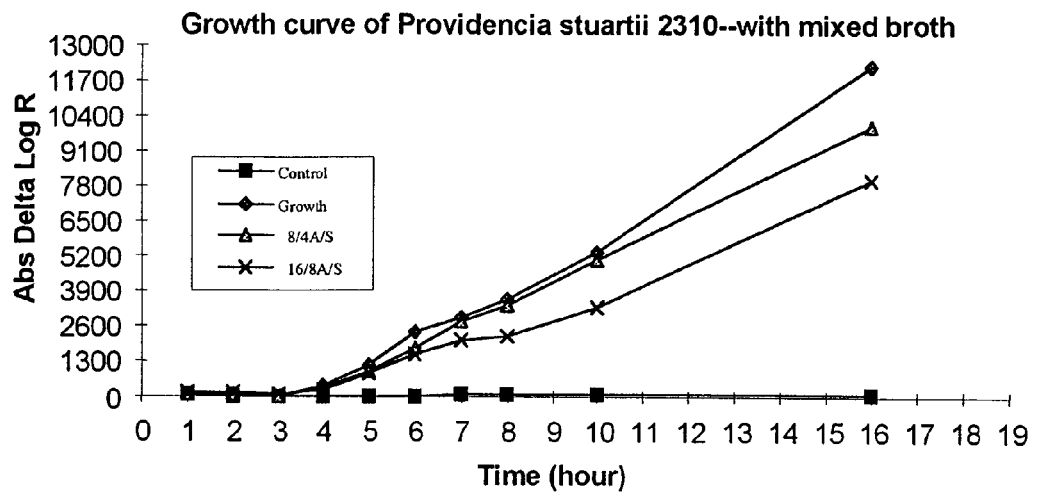
FIG. 4 illustrates growth curves with mixed broth in accordance with the teachings of the present invention.
Figure 4:
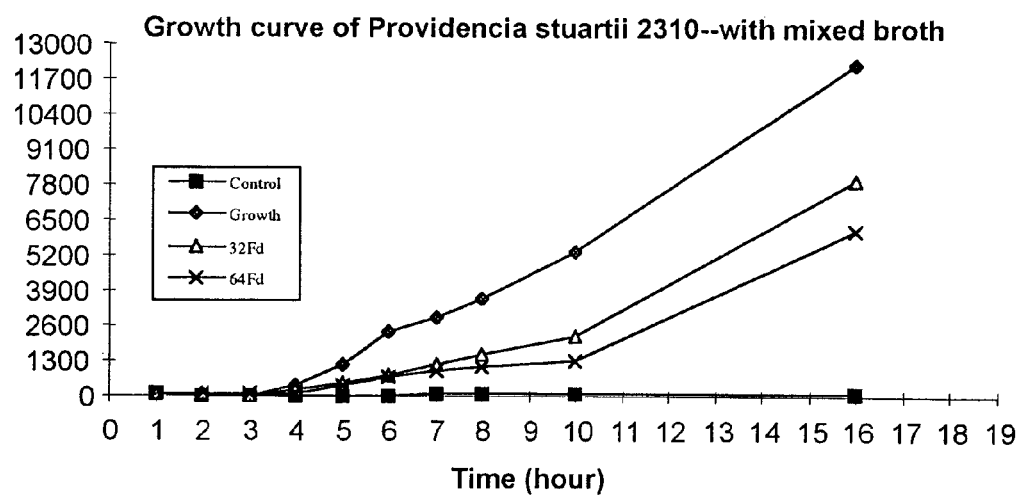

The new AST method compares growth at some time to its initial condition within each drug well. The ideal initial condition in the dried panel occurs when the organism has not yet grown and the broth is rehydrated and mixed completely. For Gram negative broth, most organisms start to grow at about two hours but the broth is not completely mixed until four hours. FIGS. 3 and 4 show the growth curves of *Providencia stuartii* 2310 in no mixed and mixed broth. The no mix broth is the standard panel set up, and the mixed broth was stirred with a sterile pipette tip 3-5 times in a circular motion.

In the mixed broth with ampicillin/sulbactam, nitrofurantoin, and cefpodoxime, the organism starts to grow about two hours earlier than in the no mix broth. We conducted similar analyses of the growth curves of *Staph. epidermidis* 123 in no mixed and mixed broth. In the mixed broth with chloramphenicol, gentamicin, and clindamycin, growth is strong and can be easily detected at six hours compared to very small growth in the no mixed broth.

Our results indicated that complete admixing of the broth substantially reduces the amount of time needed to provide useful data. Thus, while previous systems set initial and final reads to be at three and six hours, if the broth is completely mixed, growth can be easily determined between two and five hours.

EXAMPLES

Example 1

Standard Turbidimetric Assay Protocol 1

Gram Positive Assays

Although the following procedure relates to the use OF MICROSCAN® Dried Gram Positive MIC/Combo and Dried Gram Positive Breakpoint Combo panels, it is intended to be exemplary and not limiting. The standard turbidimetric assay protocol described herein is summarized below for the purpose of example but may be viewed in greater detail in the "DADE® MICROSCAN® Dried Gram Positive Procedural Manual," Dade International Inc., West Sacramento, Calif. 95691 (1997), the disclosures of which are incorporated by reference herein.

The antimicrobial susceptibility tests are dehydrated miniaturizations of the broth dilution susceptibility test. Various antimicrobial agents are diluted in Mueller-Hinton broth with calcium and magnesium or Mueller-Hinton broth with additional supplementation to concentrations bridging the range of clinical interest.

For other specific tests, the use of different broths may be appropriate. For example, oxacillin broth is supplemented with sodium chloride. Synergy screens (i.e., test methods used to evaluate combinations of antimicrobial drugs) utilize dextrose phosphate broth. Sulfamethoxazole and Trimethoprim/Sulfamethoxazole broth contain thymidine phosphorylase to reduce thymidine levels in the medium.

After inoculation and rehydration with a standardized suspension of organism and incubation at 35° C. for 16 hours (or longer if the organism requires), the MIC or a qualitative susceptibility (susceptible, intermediate or resistant) for the test organism is determined by observing the lowest antimicrobial concentration showing inhibition of growth. (See, e.g., Dried Gram Positive Procedural Manual, supra, at page 1 (and references cited therein).) Appropriate specimens should be collected, transported, and placed on primary isolation media according to procedures recommended in the Manual of Clinical Microbiology (Murray, et al. (eds.), *Manual of Clinical Microbiology*, 6th ed., American Society for Microbiology, Washington, D.C. (1995)). Subsequently, a standard, automated assay may thus be conducted essentially as follows.

A. Panel Preparation

Remove the panels to be used for storage. Panels should not be used if the desiccant is not present or if any tears or punctures compromise the integrity of the packaging.

Cut open the pouch and remove the panel. If stored in the refrigerator, remove the panel immediately from the foil pouch. Allow panels to equilibrate to room temperature prior to rehydration. Panels may be stacked with a clean cover tray on top. All opened panels should be used within the same day or discarded.

B. Inoculum Preparation

NCCLS recommends periodically checking inoculum densities by performing colony counts, refer to NCCLS document M7-A4 ("Methods for Dilution antimicrobial Susceptibility Tests for Bacteria that Grow aerobically," *Approved Standard M7-A*4, National Committee for Clinical Laboratory Standards, Wayne, Pa. (1997)). The expected results should be between $4-7 \times 10^5$ CFU/mL.

1. Turbidity Standard Technique-Primary Inoculum Method

The turbidity standard technique is recommended for direct inoculation of all aerobic gram positive cocci or for detection of methicillin resistant staphylococci.

Using a sterile wood applicator stick or bacteriological loop, touch the surface of 4-5 large or 5-10 small, morphologically similar, well-isolated colonies from an 18-24 hour non-inhibitory agar plate.

Emulsify in 3 mL of Inoculum Water (autoclaved deionized water) or 0.85% sterile saline. The final turbidity should be equivalent to that of a 0.5 McFarland Barium Sulfate turbidity standard. Cap tightly.

Vortex the suspension for 2-3 seconds. Pipet 0.1 mL (100 µL) of the standardized suspension into 25 mL of Inoculum Water with PLURONIC. Cap tightly. Invert 8-10 times to mix.

2. PROMPT® System

The PROMPT® Inoculation System may be used for the more rapidly growing gram positive cocci. Refer to the PROMPT® inoculation procedural manual for the proper use of the PROMPTS system.

It is recommended that this system be used with caution. Under-inoculation may occur with organisms that do not meet the size requirement; under-inoculation could cause incorrect susceptibility and identification test results.

3. Log Phase Technique

The log phase technique, whereby the bacterial suspension is brought to the equivalent turbidity of a 0.5 McFarland standard before dilution to the desired concentration is recommended for relatively slower growing bacterial or for those specimens which arrive late in the day.

Using a sterile wooden applicator stick or bacteriological loop, touch the surface of 4-5 large or 5-10 small, morphologically similar, well-isolated colonies from an 18-24 hour non-inhibitory agar plate. Emulsify in 4 mL of Pos Inoculum Broth and incubate at 35° C. for 2-4 hours. This is referred to as the log phase of the bacterial suspension.

Following incubation and prior to inoculation of the panel, re-vortex the suspension for 2-3 seconds. Using Pos Inoculum Broth, dilute the log phase suspension to an equivalent turbidity standard.

Pipet 0.1 (100 µL) of the standardized suspension into 25 mL of Inoculum Water with PLURONIC. Cap tightly. Invert 8-10 times to mix.

4. Stationary Phase Technique

The stationary phase technique is used for rapidly growing gram positive cocci. For the detection of methicillin resistant staphylococci the turbidity standard technique is recommended.

Using a sterile wooden applicator stick or bacteriological loop, touch the surface of 4-5 large or 5-10 small, morphologically similar, well-isolated colonies from an 18-24 hour non-inhibitory agar plate. Emulsify the colonies in 0.5 ml Pos Inoculum Broth (Todd-Hewitt Broth). Cap tightly.

Vortex the suspension for 2-3 seconds. Loosen the tube cap and incubate for 4-6 hours at 35° C. Following incubation and prior to inoculation of the panel, re-vortex the suspension for 2-3 seconds. If the broth is turbid after incubation, transfer 0.01 mL (10 µL) of the suspension into 25 ml of Inoculum Water (autoclaved water with PLURONIC). Cap tightly. Invert the tube 8-10 times to mix.

If the broth is not turbid after 6 hours incubation, incubate for an additional 12-18 hours prior to panel inoculation. Alternately, the turbidity standard technique can be used. If broth is turbid after the additional 12-18 hours of incubation, inoculate the 25 mL of Inoculum Water as directed in the paragraph immediately above.

C. Panel Rehydration/Inoculation

Rehydration and inoculation of dried panels may readily be performed using commercially-available devices such as the RENOK rehydration/inoculator available from Dade MicroScan Inc. (West Sacramento, Calif.). The RENOK rehydrator/inoculator is a manual multi-channel pipette that simultaneously rehydrates and inoculates MICROSCAN® panels. It is used in conjunction with MICROSCAN® disposable inoculator sets. An inoculator set generally consists of a seed trough to contain the inoculum and a transfer lid to dispense the inoculum. The RENOK operates by drawing in a controlled amount of air and creating a vacuum when the center lever is lifted. The vacuum draws inoculum from the seed trough into the transfer lid. Inoculum does not enter the RENOK unit so it does not become contaminated.

The inoculum-filled transfer lid is then placed over a MICROSCAN® panel. The inoculum is released into the panel by pressing the release button. The panel is rehydrated with the bacterial inoculum and is thus simultaneously rehydrated and inoculated. (For further details, see the Renok Operator's Manual or the DADE® MICROSCAN® Microbiology Manual, both available from Dade MicroScan Inc., West Sacramento, Calif., the disclosures of which are incorporated by reference herein.) As noted above, however, the within-described system is exemplary and not limited; the methods and compositions of the present invention may be utilized in and with other systems known in the art, including other commercially-available systems.

In the present example, rehydration and inoculation are performed according to the instructions contained in the RENOK operator's manual. If an alternate system is used, rehydrate with 115±10 µL OF Inoculum Water (PLURONIC). A final well concentration of $4\text{-}7 \times 10^5$ CFU/mL is preferably achieved.

To ensure viability and purity of the organism, a purity plate may be prepared by streaking the inoculum to a blood agar plate and incubate overnight. If two or more colony types are present on the purity plate, re-isolate the colonies and retest.

D. Biochemical Overlays

Using a dropper bottle, overlay the ARG and URE wells with at least 3 drops of mineral oil. (These wells are underlined on the panel.) The media in the wells must be completely covered with mineral oil, but the oil should not overflow the wells.

E. Incubation

To ensure even thermal distribution during incubation, stack the panels in groups of 3-5. Place a clean cover tray on top of each group of panels to prevent evaporation. Cover trays may be reused. Do not decontaminate the cover trays with alcohol. They may be cleaned with soap and water. Rinse well and allow to air dry. Incubate the panels for 16-24 hours at 35° C. in a non-$CO_2$ incubator.

F. Reading the Panels

The panels may be read manually (e.g. using a a MICROSCAN® Microdilution Viewer, Dade MicroScan Inc., West Sacramento, Calif.) and results recorded on an appropriate worksheet. The panels may also—or alternatively—be read instrumentally, e.g., using a TOUCHSCAN®-SR, AUTOSCAN® 4, or WALKAWAY® system (Dade MicroScan Inc., West Sacramento, Calif.). Refer to the appropriate operator's manual for reading panels using instrumentation; one may also wish to refer to the "Dried Gram Positive Procedural Manual" (Id.). Quality control methods are also included in the latter manual, incorporated herein by reference.

G. Interpretation Of MIC Results

Susceptibility is determined by comparing the MIC of an organism to the attainable blood or urine level of the antimicrobic. Interpretative criteria as indicated in NCCLS document M100-S7 are provided in the aforementioned procedural manual.

Example 2

Standard Turbidimetric Assay Protocol 2

Gram Negative Assays

Although the following procedure relates to the use of MICROSCAN® Dried Gram Negative MIC/Combo and Dried Gram Negative Breakpoint Combo panels, it is intended to be exemplary and not limiting. The standard turbidimetric assay protocol described herein is summarized below for the purpose of example but may be viewed in greater detail in the "DADE® MICROSCAN® Dried Gram Negative Procedural Manual," Dade International, Inc., West Sacramento, Calif. (1996), the disclosures of which are incorporated by reference herein.

The antimicrobial susceptibility tests are dehydrated miniaturizations of the broth dilution susceptibility test. Various antimicrobial agents are diluted in Mueller-Hinton broth with calcium and magnesium or Mueller-Hinton broth with additional supplementation to concentrations bridging the range of clinical interest. Breakpoint Combo panels use concentrations equivalent to the categorical breakpoints of NCCLS. Trimethoprim, Sulfamethoxazole and Trimethoprim/Sulfamethoxazole broth contain thymidine phosphorylase to reduce thymidine levels in the medium.

After inoculation and rehydration with a standardized suspension of organism and incubation at 35° C. for 16 hours (or longer if the organism requires), the MIC for the test organism is determined by observing the lowest antimicrobial concentration showing inhibition of growth. (see, e.g., Dried Gram Negative Procedural Manual, supra, at page 1 (and references cited therein).) Appropriate specimens should be collected, transported, and placed on primary isolation media according to procedures recommended in the Manual of Clinical Microbiology (Murray, et al. (eds.), *Manual of Clinical Microbiology*, 6th ed., American Society for Microbiology, Washington, D.C. (1995)). Subsequently, a standard, automated assay may thus be conducted essentially as follows.

A. Panel Preparation

1. Remove the panels to be used from storage. Panels should not be used if the desiccant is not present or if the integrity of the packaging is compromised.

2. Cut open the pouch and remove the panel. If stored in the refrigerator, remove the panel immediately from the foil pouch. Allow panels to equilibrate to room temperature prior to rehydration. Panels may be stacked with a clean cover tray on top. All opened panels should be used within the same day or discarded.

B. Inoculum Preparation

NCCLS recommends periodically checking inoculum densities by doing colony counts. Refer to NCCLS document M7-A3. The expected results should be between $4\text{-}7\times10^5$ CFU/mL.

1. Turbidity Standard Technique-Primary Inoculation Method

The turbidity standard technique is recommended for direct inoculation of all aerobic gram-negative bacilli.

Using a sterile wooden applicator stick or bacteriological loop, touch the surface of 4-5 large or 5-10 small, morphologically similar, well-isolated colonies from an 18-24 hour non-inhibitory agar plate. Emulsify in 3 mL of Inoculum Water (autoclaved distilled water). The final turbidity should be equivalent to that of a 0.5 McFarland Barium Sulfate Turbidity Standard. Cap tightly.

Vortex the suspension for 2-3 seconds. Pipet 0.1 mL (100 µL) of the standardized suspension into 25 mL of Inoculum Water with PLURONIC. Cap tightly. Invert 8-10 times to mix.

2. PROMPT® System

The PROMPT® Inoculation System may be used to inoculate gram-negative bacilli. Refer to the procedural manual for the proper use of the PROMPT® system.

3. Log Phase Technique

The log phase technique, whereby the bacterial suspension is brought to the equivalent turbidity of a 0.5 McFarland Barium Sulfate Turbidity Standard before dilution to the desired concentration, is recommended for relatively slower growing bacteria or for those specimens which arrive late in the day.

Using a sterile wooden applicator stick or bacteriological loop, touch the surface of 4-5 large or 5-10 small, morphologically similar, well-isolated colonies from an 18-24 hour non-inhibitory agar plate. Emulsify in 4 mL of BHI Broth (Brain Heart Infusion broth; commercially available, e.g., from the Remel Catalog (REMEL; Lenexa, Kans.)) and incubate at 35° C. for 2-4 hours. This is referred to as the log phase of the bacterial suspension.

Following incubation and prior to inoculation of the panel, re-vortex the suspension for 2-3 seconds. Using BHI Broth, dilute the log phase suspension to an equivalent turbidity of the 0.5 McFarland standard. Pipet 0.1 mL (100 µL) of the standardized suspension into 25 mL of Inoculum Water with PLURONIC. Cap tightly. Invert 8-10 times to mix.

4. Stationary Phase Technique

The stationary phase technique is recommended for use with rapidly growing gram-negative bacilli. The procedure is conducted essentially as follows.

Using a sterile wooden applicator stick or bacteriological loop, touch the surface of 4-5 large or 5-10 small, morphologically similar, well-isolated colonies from an 18-24 hour non-inhibitory agar plate. Emulsify the colonies in 0.5 mL Brain Heart Infusion (BHI) broth. Cap tightly.

Vortex the suspension for 2-3 seconds. Loosen the tube cap and incubate for 4-6 hours at 35° C. Following incubation and prior to inoculation of the panel, re-vortex the suspension for 2-3 seconds. If the broth is turbid after incubation, transfer 0.01 mL (10 µL) of the suspension into 25 mL of Inoculum Water with PLURONIC. Cap tightly. Invert the tube 8-10 times to mix.

C. Oxidase Test

Perform an oxidase test prior to inoculating the panels. Record results in the appropriate space on the worksheet or as requested by the instrumentation. The recommended oxidase reagent is tetramethyl-p-phenylene-diamine-dihydrochloride.

D. Panel Rehydration/Inoculation

Rehydration and inoculation is performed using the RENOK system with Inoculators-D.

Refer to the RENOK operator's manual for use. If an alternate system is used, rehydrate with 115 µl±10 µl of Inoculum Water (PLURONIC). A final well concentration of $4\text{-}7\times10^5$ CFU/mL should be achieved. To ensure viability and purity of the organism tested a purity plate may be prepared by streaking the inoculum to a blood agar plate and incubate for 16-20 hours. If two or more colony types are present on the purity plate, reisolate the colonies and retest.

E. Biochemical Overlays

Using a dropper bottle, overlay the GLU, URE, $H_2S$, LYS, ARG, ORN and DCB with 3 drops of mineral oil. (These wells are underlined on the panel.) The media in the wells must be completely covered with mineral oil, but the oil should not overflow the wells.

F. Seal Strip

For oxidase positive organisms only, place a seal strip over the CIT, MAL, ONPG, TAR, ACE, CET, OF/G, OF/B and DCB wells. The quarter-inch locator hole in the tape should be aligned over the DCB well. For WALKAWAY® systems, the lid is used in lieu of a seal strip. (See, e.g., U.S. Pat. No. 4,719,087, the disclosure of which is incorporated by reference herein.)

G. Incubation

To ensure even thermal distribution during incubation, stack the panels in groups of 3-5.

Place a clean cover tray on top of each group of panels to prevent evaporation. (Cover trays may be reused.) Do not decontaminate cover trays with alcohol; they may be cleaned with soap and water. Rinse well and allow to air dry. Incubate the panels for a minimum of 16 hours at 35° C. in a non-$CO_2$ incubator.

H. Reading the Panels

The panels may be read manually (e.g. using a MICROSCAN® Microdilution Viewer, Dade MicroScan Inc., West Sacramento, Calif.) and results recorded on an appropriate worksheet. The panels may also—or alternatively—be read instrumentally, e.g., using a TOUCHSCAN®-SR, AUTOSCAN®-4, or WALKAWAY® system (Dade MicroScan Inc., West Sacramento, Calif.). Refer to the appropriate operator's manual for reading panels using instrumentation.

Guidelines for reading antimicrobic susceptibilities are available in the art and in relevant instruction manuals; see, e.g., the Dade MICROSCAN® Dried Gram Negative Procedure Manual at pages 11-12. Quality control methods are also included in the latter manual, which is incorporated herein by reference.

Example 3

Fluorescent ID Procedure

Although the following procedure relates to the use of MICROSCAN® Rapid Panels, it is intended to be exemplary and not limiting. The standard fluorescent ID protocol described herein is summarized below for the purpose of example but may be viewed in greater detail in the "Dade MICROSCAN® Rapid Gram Positive Procedural Manual," Dade Behring Inc., West Sacramento, Calif. (1998), the disclosures of which are incorporated by reference herein.

The antimicrobial susceptibility tests are dehydrated miniaturizations of the broth dilution susceptibility test. Various antimicrobial agents are serially diluted in autoclaved distilled water with fluorogenic compounds to concentrations bridging the range of clinical interest. Trimethoprim/Sulfamethoxazole contains thymidine phosphorylase to reduce thymidine levels in the medium.

Fluorogenic substrates or fluorometric indicators are used for the identification of *Micrococcaceae, Streptococcaceae, Listeria monocytogenes*, and *Aerococcus viridans*.

Identification is based on hydrolysis of fluorogenic substrates, pH changes following substrate utilization, production of specific metabolic byproducts, or the rate of production of specific metabolic byproducts after 2 hours incubation at 35° C. in the WALKAWAY® Systems (Id. at page 1-1).

Appropriate specimens should be collected, transported, and placed on primary isolation media according to procedures recommended in the Manual of Clinical Microbiology (Murray, et al. (eds.), *Manual of Clinical Microbiology*, 6th ed., American Society for Microbiology, Washington, D.C. (1995)). Subsequently, a standard, automated assay may thus be conducted essentially as follows.

A. Panel Preparation

Remove the panels to be used from storage. Panels should not be used if the desiccant is not present or if the integrity of the packaging is compromised (unsealed, punctured, or torn). Tear open the pouch at the notch and remove the panel. Allow panels to equilibrate to room temperature prior to rehydration. Panels may be stacked with a clean cover tray on top.

B. Inoculum Preparation

Using sterile wooden applicator stick or bacteriological loop, touch the surface of 4-5 large or 5-10 small, morphologically similar, well-isolated colonies from an 18-24 hour Trypticase Soy with 5% sheep blood agar plate. Emulsify in 6.5 mL of 0.4% saline with PLURONIC. To ensure an even distribution of the bacterial growth in the saline with PLURONIC, rub the stick or loop on the bottom or side of the tube. This will reduce "clumping" and will aid in emulsification of mucoid growth.

The final turbidity should be equivalent to that of a 0.5 McFarland Barium Sulfate Turbidity Standard. The comparison of the saline with PLURONIC and the McFarland standard should be done using a nephelometer or an adequate light source by comparing the tubes to a white card with contrasting black lines. Cap tightly.

Vortex the suspension for 2-3 seconds. Pipet 300 µL (0.3 mL) of the standardized saline suspension into 25 mL of Rapid Pos Inoculum Broth. Invert 8-10 times to mix. Retain the remaining 6.2 mL of the standardized saline suspension.

C. Panel Rehydration/Inoculation

Rehydration and inoculation is performed using the MICROSCAN® RENOK Rehydrator/Inoculator system with Inoculators-R. Remove the transfer lid from the inoculator set. Pour the 25 mL Rapid Pos Inoculum broth into the top portion of the seed trough and the 6.2 mL standardized saline suspension into the bottom portion of the seed trough. Replace the transfer lid and attach the RENOK Rehydrator/Inoculator. Refer to the RENOK Rehydrator/Inoculator Operators Manual for use.

If an alternate system is used, rehydrate each well with 115 µL±10 µL CFU/mL of the appropriate suspension. The final well concentration in the identification substrates should be $1.5 \times 10^8$ CFU/mL and in the antimicrobial agents should be $1.8 \times 10^8$ CFU/mL.

D. Incubation

Label each panel with a WALKAWAY® System bar code label and place a WALKAWAY® System tray lid on each panel. Insert panels into any available open slot in the WALKAWAY® System. Refer to the WALKAWAY® System Operator's manual for use. Panels are incubated for a maximum of 15 hours prior to final reading.

E. Reading the Panels

The WALKAWAY® System reads the identification substrates after 2 hours incubation at 35° C. MIC readings are made at 3.5, 4.5, 5.5, 7, 8, 11 and 15 hours. Refer to the WALKAWAY® System Operator's Manual for use.

Changes in intensity of fluorescence are used as an indication of positivity or negativity of identification substrates. Further details regarding identification substrates and organism identification are available in the literature accompanying the instrumentation used. (See, e.g., "Rapid Gram Positive Procedural Manual," Dade MicroScan Inc., West Sacramento, Calif. (1998), the disclosures of which are incorporated by reference herein.)

Example 4

Hybrid Panels and Related Devices

Although the following procedure relates to the use of MICROSCAN® Rapid Pos ID Panels, it is intended to be exemplary and not limiting. The standard fluorescent and non-fluorescent protocols described above are all useful in the determination of the MIC and ID of samples to be tested.

The following fluorescent ID protocol described herein is particularly useful in hybrid panels and is summarized below for the purpose of example. The protocol may be viewed in greater detail in the "DADE® MICROSCAN® Rapid Gram Positive Identification Procedural and QC Manual," Dade Behring Inc., West Sacramento, Calif. (1998), the disclosures of which are incorporated by reference herein.

Fluorogenic substrates or fluorometric indicators are used for the identification of *Micrococcaceae, Streptococcaceae, Listeria monocytogenes*, and *Aerococcus viridans*. Identification is based on hydrolysis of fluorogenic substrates, pH changes following substrate utilization, production of specific metabolic byproducts, or the rate of production of specific metabolic byproducts after 2 hours incubation at 35° C. in the WALKAWAY® Systems (Id. at page 1-1).

Appropriate specimens should be collected, transported, and placed on primary isolation media according to procedures recommended in the Manual of Clinical Microbiology (Murray, et al. (eds.), *Manual of Clinical Microbiology*, 6th ed., American Society for Microbiology, Washington, D.C. (1995)). Subsequently, a standard, automated assay may thus be conducted essentially as follows.

A. Panel Preparation

Remove the panels to be used from storage. Panels should not be used if the desiccant is not present or is broken or if the integrity of the packaging is compromised (unsealed, punctured or torn). Tear open the pouch at the notch and remove the panel. Allow panels to equilibrate to room temperature prior to rehydration. Panels may be stacked with a clean cover tray on top.

B. Inoculum Preparation

Using a sterile wooden applicator stick or bacteriological loop, touch 4-5 large or 5-10 small, morphologically similar, well-isolated colonies from an 18-24 hour TSA+5% sheep blood agar plate. Disperse in 6.5 mL or 0.4% saline with PLURONIC. The final turbidity should be equivalent to that of a 0.5 McFarland Barium Sulfate Turbidity Standard. Cap tightly. Vortex the suspension for 2-3 seconds.

C. Panel Rehydration/Inoculation

Rehydration and inoculation is performed using the MICROSCAN® RENOK rehydrator/inoculator system with Inoculator-R. Remove the transfer lid from the inoculator set. Pour the 6.5 mL standardized saline suspension into the bottom portion (3 rows) of the divided seed trough. Pour 25 mL of uninoculated Inoculum Water with PLURONIC-D into the top portion (5 rows) of the seed trough.

Replace the transfer lid and attach the RENOK rehydrator/inoculator. Refer to the RENOK rehydrator/inoculator Operator's Manual for use. If an alternate system is used, rehydrate each well with 115 µl±10 µl of the appropriate suspension. The final well concentration in the identification substrates should be $1.5 \times 10^8$ CFU/mL.

D. Incubation

Label each panel with a WALKAWAY® System bar code label and place a WALKAWAY® System tray lid on each panel. Insert panels into any available open slot in the WALKAWAY® System. Refer to the WALKAWAY® System Operator's Manual for use. Panels are incubated for 2 hours prior to final reading.

E. Reading the Panels

The WALKAWAY® System reads the identification substrates after 2 hours incubation at 35° C. Changes in intensity of fluorescence are used as an indication of positivity or negativity of identification substrates.

Further information regarding the principles of reactions, organism identification, expected values, and limitations is available in the relevant manual accompanying the instrumentation used. (see, eg., The "DADE® MICROSCAN®-Rapid Gram Positive Identification Procedural and QC Manual," Dade Behring Inc., West Sacramento, Calif. (1998), the disclosures of which are incorporated by reference herein.)

Example 5

Assays of Enterobacteriaceae Samples

The new MICROSCAN® AST System combines early (5-6 hr) MIC results with the ability to hold and read panels incrementally up to 24 hours. AST results are determined using standard MICROSCAN® Dried Overnight Panels that can also be read manually. This feasibility study evaluated the test system for 23 antimicrobics using preliminary algorithms against a NCCLS frozen reference microdilution panel. Test isolates included 147 stock cultures belonging to the family Enterobacteriaceae with known variable resistance patterns. Cultures were prepared and tested according to standard protocols for Gram-negative cultures (see Example 2 above).

Antimicrobics tested included four Aminoglycosides, six cephems, eight quinolones, aztreonam, meropenem, nitrofurantoin, trimethoprim, and trimethoprim/sulfamethoxazole. Examples of antimicrobics useful as disclosed herein are known to those of skill in the art and include those listed in the various reference manuals cited herein.

Total essential agreement between the test system and the reference method was 96.1% (3249/3381 organism-antimicrobic combinations) using preliminary algorithms and was greater than 95% for all antimicrobics except ceftazidime, cephalothin, cefpodoxime, aztreonam, and trimethoprim. As used herein essential agreement" means that the dilution in which growth occurs is within one dilution of the reference MIC.

For the purpose of illustration only, in the following exemplary chart, where a closed circle (•) represents growth and an open circle (○) represents no growth, one may readily observe the difference between results considered to be in essential agreement" vs. those that are not (i.e. the results labeled "out").

| Dilution | | | | | |
|---|---|---|---|---|---|
| 1 | 2 | 3 | 4 | 5 | |
| • | • | • | ○ | ○ | Reference |
| • | • | ○ | ○ | ○ | "Essential Agreement" |
| • | • | • | • | ○ | "Essential Agreement" |
| • | ○ | ○ | ○ | ○ | "Out" |
| • | • | • | • | • | "Out" |

The total category error rate for all antimicrobics was 2.2%—i.e. 1.2% very major errors, 0.2% major errors, and 0.8% two-dilution minor errors. Total category error rates were 0% for meropenem, 0.4% for the eight quinolones, 0.7% for trimethoprim/sulfamethoxazole, 1.4% for nitrofurantoin, 1.9% for the four aminoglycosides, 2.7% for trimethoprim, 4.5% for the six cephems, and 6.8% for aztreonam. These preliminary data demonstrate the feasibility of the new MICROSCAN® AST System when compared to a frozen microdilution panel.

Example 6

Assays of Stock Enterobacteriaceae Samples

The new MICROSCAN® AST System combines early (5-6 hr) MIC results with the ability to hold and read panels incrementally up to 24 hours. AST results are determined using standard MICROSCAN® Dried Overnight Panels that can also be read manually. Cultures were prepared and tested according to standard protocols for Gram-negative cultures (see Example 2 above).

This analysis was conducted to evaluate the accuracy of the new system with preliminary algorithms in comparison to a frozen NCCLS frozen reference microdilution panel. Testing included 376 gram-negative stock Enterobacteriaceae with the following antimicrobics: amoxicillin K clavulanate, ampicillin, ampicillin/sulbactam, carbenicillin, piperacillin, piperacillin/tazobactam, ticarcillin, ticarcillin/K clavulanate, and tetracycline.

Total essential agreement between the test system and the reference method was 90.9% (3076/3384 organism-antimicrobic comparisons) and ranged from 83.8% for augmentin to 97.1% for ampicillin/sulbactam. The total category error rate was 5.9%—i.e. 1.5% very major errors, 0.3% major errors, and 4.1% two-dilution minor errors. Very major error rates ranged from 0.3% for carbenicillin to 3.7% for amoxicillin/K clavulanate. Major error rates ranged from 0% for carbenicillin, ticarcillin, and ticarcillin/K clavulanate, to 1.3% for tetracycline.

This preliminary study demonstrates that the new AST system gives good correlation for enteric bacteria when compared to a frozen reference microdilution panel with these antimicrobics.

Example 7

Validation of AST System with Gram-Negative Bacteria

The new MICROSCAN® AST System combines early (5-6 hr) MIC results with the ability to hold and read panels incrementally up to 24 hours. AST results are determined using standard MICROSCAN® Dried Overnight Panels that can also be read manually. This preliminary study was conducted to evaluate the accuracy of the new system with preliminary algorithms in comparison to a frozen NCCLS reference microdilution panel. Testing included 485 gram-negative stock isolates with known variable resistance patterns and included the following antimicrobics: cefamandole, cefazolin, cefepime, cefixime, cefonicid, ceftizoxime, cefuroxime, and chloramphenicol. Cultures were prepared and tested according to standard protocols for Gram-negative cultures (see Example 2 above).

Total essential agreement between the test system and the reference method was 94.0% (3649/3880 organism-antimicrobic comparisons) and ranged from 87.6% for cefazolin to 95.9% for cefepime and cefixime. The total category error rate with the new test system was 3.6%—i.e., 1.6% very major errors, 0.7% major errors, and 1.3% two-dilution minor errors. Very major error rates ranged from 0.4% for chloramphenicol and cefepime to 3.5% for cefaclor. Major error rates ranged from 0% for cefazolin to 1.6% for chloramphenicol. This study shows the new MICROSCAN® AST system for gram-negative bacteria gives good correlation in comparison to a frozen microdilution panel with the antimicrobics tested.

Example 8

Validation of AST System with Gram-Positive and Gram-Negative Isolates

The new MICROSCAN® AST System combines early (5-6 hr) MIC results with the ability to hold and read panels incrementally up to 24 hours. AST results are determined using standard MICROSCAN® Dried Overnight Panels that can also be read manually.

Feasibility studies were conducted using 143 recently-obtained clinical isolates. The study included 83 gram-positive isolates (58 *Staphylococci*, 24 *Enterococci*, 1 *Viridans streptococci*) and 60 gram-negative isolates including 21 nonfermenters. Cultures were prepared and tested according to standard protocols for Gram-positive and Gram-negative cultures (see Examples 1 and 2 above).

The AST panels tested were Pos MIC Type 10, Neg/Urine MIC Type 7 and Neg MIC Plus Type 3 with 29 gram-positive and 35 gram-negative antimicrobics evaluated. Results were obtained using research software in the WALKAWAY® system. Instrument results obtained at early time points were compared to instrument results obtained after appropriate overnight incubation, 18 or 24 hours.

Overall, preliminary results obtained for the 83 gram-positive isolates show 71% of the panels completed at 6 hours with 93% categorical agreement to overnight results. For the 60 gram-negative isolates, 85% of the panels completed at 5 hours with 91% categorical agreement. Optimization during development will further improve the agreement between early read times to the overnight method. These data prove the feasibility of the new MICROSCAN® AST System allowing for early, accurate reads with an option of overnight incubation.

Example 9

Validation of Hybrid Assay System and Use of Clear Panels

The new MICROSCAN® AST System combines early (5-6 hr) MIC results with the ability to hold and read panels incrementally up to 24 hours. AST results are determined using standard clear MICROSCAN® Dried Overnight Panels and thus can also be read manually. The current Rapid Gram-Negative Identification 3 (RNID3) system is comprised of 36 fluorescent biochemical tests in a white plastic panel. Cultures and panels were prepared and tested according to the protocols set forth in herein (see Examples 3 and 4 above).

To combine these systems, RNID3 is converted for use in clear panels. An identification study was conducted to evaluate the agreement of identifications obtained on 110 gram-negative bacteria. Bacteria were tested with the RNID3 substrates on both clear and white panels. A total of 44 biochemical interpretations were generated for each strain, for a total of 4840 interpretations for each panel type.

We obtained 96.9% (4690/4840) agreement of interpretations between panel types. Data analysis showed that the 3.1% (150/4840) that did not agree were variable reactions, and had no impact on the accuracy or performance when comparing the predicted identification (clear panel) to the target identification (white panel). Feasibility performance of the RNID3 system in clear panels demonstrates excellent correlation in comparison to the current RNID3 system in white panels.

We claim:

1. A method for high throughput concurrent microorganism identification and antimicrobial susceptibility testing comprising:
   a) inoculating one or more clear plastic panels having a plurality of wells with a sample to be tested for microorganism identification and antimicrobial susceptibility, wherein the one or more panels comprise a plastic microtiter plate having an opaque top surface and clear plastic wells for determining a microorganism's identification and a microorganism's susceptibility to at least one antimicrobial agent;
   wherein the plurality of wells comprises at least one growth well, at least one minimum-inhibitory concentration (MIC) antimicrobial test well, and at least one control well;
   wherein for microorganism identification, the at least one growth well contains an assay reagent, which when acted upon by a microorganism, is indicative of a microorganism family, genus and/or species;
   wherein for antimicrobial susceptibility testing, the at least one MIC antimicrobial test well contains an antimicrobial agent;
   b) placing the inoculated one or more clear plastic panels into an apparatus that maintains the inoculated one or more clear plastic panels at a predetermined temperature for a predetermined time;
   c) incubating the inoculated one or more clear plastic panels in the apparatus at the predetermined temperature for a first predetermined time;
   d) at a second predetermined time, performing a bichromatic collection process comprising:
      i) transmitting a visible light wavelength through the at least one growth well,
      ii) transmitting a fluorescent light wavelength through the at least one growth well using a read frame having a width optimized for use with clear plastic wells, wherein the visible light wavelength and the fluorescent light wavelength are distinct,
      iii) collecting resulting visible light signals from the at least one growth well and converting the resultant visible light signals into a growth well turbidity reading, and
      iv) collecting resultant fluorescent light signals from the at least one growth well using the read frame and converting the resultant fluorescent light signals into a growth well fluorescent reading;
   e) determining the identity of the microorganism from the growth well turbidity reading and the growth well fluorescent reading;
   f) determining the susceptibility of the microorganism to the antimicrobial agent in each of the at least one MIC antimicrobial test well by performing the following steps for each respective MIC antimicrobial test well:
      i) setting read times for turbidity;
      ii) setting thresholds for well growth;
      iii) at a first read time, determining if a respective control well has growth;
      iv) if the answer to iii) is yes, then recording a first turbidity reading from the respective control well and returning the plate to incubation;
      v) if the answer to iii) is no, then returning the plate to incubation;
      repeating steps vi)-viii) until a maximum read time is reached:
      vi) at a next read time, determining if the respective control well has growth;
      vii) if answer to vi) is yes, then recording a second turbidity reading from the respective control well and if the second turbidity reading is higher than the first turbidity reading and the second turbidity reading reached a first threshold for well growth, then recording the respective control well as growth;
      viii) if the answer to vi) is no, then returning the plate to incubation;
      ix) if the respective control well was recorded as growth in step vii), then determining if the respective MIC antimicrobial test well if has growth;
      x) if the answer to ix) is yes, then determining and recording the turbidity of a respective growth well and the respective MIC antimicrobial test well and determine a ratio of turbidity of the respective MIC antimicrobial test well to turbidity of the respective growth well;
      xi) if the ratio of step x) exceeds a threshold ratio level, then returning the plate to incubation;
      xii) if the ratio of step x) is less than the threshold ratio level, then recording the concentration of the antimicrobial agent in the respective MIC antimicrobial test well as the minimum inhibitory concentration;
      xiii) recording the turbidity of the respective growth well and the turbidity of the respective antimicrobial test well at a maximum read time;
      xiv) reporting the recorded results and determining the susceptibility of the microorganism to the antimicrobial agent according to the reported results.

2. The method of claim 1 wherein the assay reagent is a growth requirement for a particular microorganism.

3. The method of claim 2 wherein the growth requirement is growth media specific for yeast, anaerobic bacteria, or fastidious bacteria.

4. The method of claim 2 wherein the growth well turbidity reading and the MIC antimicrobial test well turbidity reading are increased compared to a control well when the microorganism uses the growth requirement.

5. The method of claim 1 wherein the assay reagent is a substrate for an enzyme that is unique to a microorganism family, genus, and/or species.

6. The method of claim 5 wherein when the substrate is acted upon by the enzyme in a particular microorganism, a fluorescently detectable product is detected in step d).

* * * * *